United States Patent
Kim et al.

(10) Patent No.: US 10,047,154 B2
(45) Date of Patent: *Aug. 14, 2018

(54) ANGIOPOIETIN-2 SPECIFIC ANTIBODIES AND USES THEREOF

(71) Applicant: Samsung Electronics Co., Ltd., Suwon-si, Gyeonggi-do (KR)

(72) Inventors: Seok Kyun Kim, Seoul (KR); Sang Yeul Han, Yongin-si (KR); Kwang Hoon Lee, Osan-si (KR); Kyung Eun Kim, Yongin-si (KR); Chung Ho Kim, Yongin-si (KR); Yong In Kim, Seongnam-si (KR); Hyung-Chan Kim, Yongin-si (KR); Yoon Sook Lee, Hwaseong-si (KR); Hyo Seon Lee, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 47 days.

This patent is subject to a terminal disclaimer.

(21) Appl. No.: 14/447,242

(22) Filed: Jul. 30, 2014

(65) Prior Publication Data

US 2015/0037343 A1 Feb. 5, 2015

(30) Foreign Application Priority Data

Jul. 30, 2013 (KR) ........................ 10-2013-0090209

(51) Int. Cl.
| | | |
|---|---|---|
| *A61K 39/395* | (2006.01) | |
| *A61K 39/00* | (2006.01) | |
| *C07K 16/00* | (2006.01) | |
| *C07K 16/22* | (2006.01) | |

(52) U.S. Cl.
CPC ........ *C07K 16/22* (2013.01); *A61K 2039/505* (2013.01); *C07K 2317/21* (2013.01); *C07K 2317/34* (2013.01); *C07K 2317/622* (2013.01); *C07K 2317/76* (2013.01); *C07K 2317/92* (2013.01); *G01N 2500/04* (2013.01)

(58) Field of Classification Search
None
See application file for complete search history.

(56) References Cited

U.S. PATENT DOCUMENTS

| 5,567,440 | A | * | 10/1996 | Hubbell | ............... | A61K 9/5031 424/484 |
| 5,859,205 | A | * | 1/1999 | Adair | ..................... | C07K 16/18 530/387.1 |
| 6,365,154 | B1 | | 4/2002 | Holmes et al. | | |
| 8,133,979 | B2 | | 3/2012 | Brinkmann et al. | | |
| 2008/0267971 | A1 | | 10/2008 | Green et al. | | |
| 2010/0159587 | A1 | | 6/2010 | Brinkmann et al. | | |
| 2011/0027286 | A1 | | 2/2011 | Thurston et al. | | |
| 2012/0034237 | A1 | | 2/2012 | Boone et al. | | |
| 2012/0052073 | A1 | | 3/2012 | Green et al. | | |
| 2014/0113858 | A1 | * | 4/2014 | Han | ..................... | C07K 14/515 514/7.6 |
| 2014/0302039 | A1 | * | 10/2014 | Jeong | ..................... | C07K 16/22 424/138.1 |

FOREIGN PATENT DOCUMENTS

WO WO2012137993 * 10/2012

OTHER PUBLICATIONS

Barton et al, Structure of the Angiopoietin-2 Receptor Binding Domain and Identification of Surfaces Involved in Tie2 Recognition. Structure, vol. 13, 825-832, May 2005.*
Barton et al/ Crystal structures of the Tie2 receptor ectodomain and the angiopoietin-2-Tie2 complex. Nature Structural & Molecular Biology [2006, 13(6):524-532.*
Vajdos et al. Comprehensive functional maps of the antigen-binding site of an anti-ErbB2 antibody obtained with shotgun scanning mutagenesis. J. Mol. Biol.*
Brown et al. Tolerance of single, but not multiple, amino acid replacements in antibody VH CDR 2: a means of minimizing B cell wastage from somatic hypermutation? J. Immuno. May 1996, 3285-91.*
Rudikoff et al Single amino acid substitution altering antigen-binding specificity. Proc Natl Acad Sci U S A. Mar. 1982;79(6):1979-83.*
Felcht et al. Angiopoietin-2 differentially regulates angiogenesis through TIE2 and integrin signaling. J Clin Invest. Jun. 2012;122(6):1991-2005.*
Campbell A, General properties and applications of monoclonal antibodies, Elsevier Science Publishers, section 1.1, pp. 1-32, 1984.*
Van Regenmortel MHV. Mapping Epitope Structure and Activity: From One-Dimensional Prediction to Four-Dimensional Description of Antigenic Specificity Methods. 9(3):465-72, 1996.*
Eduardo Padlan, Anatomy of the antibody molecule. Mol Immunol. Feb. 1994;31(3):169-217.*
Paul, Fundamental Immunology, 3rd Edition, 1993, pp. 292-295.*
Lerner. Tapping the immunological repertoire to produce antibodies of predetermined specificityNature 1982; 299:592-596.*
Clark et al. An antibody loop replacement design feasibility study and a loop-swapped dimer structure. Protein Engineering, Design & Selection vol. 22 No. 2 pp. 93-101, 2009. (Year: 2009).*
Helms et al. Destabilizing loop swaps in the CDRs of an immunoglobulin VL domain. Protein Science (1995), 4:2073-2081. (Year: 1995).*
Yang, et al "CDR Walking Mutagenesis for the Affinity Maturation of a Potent Human Anti-HIV-1 Antibody into the Picomolar Range," *J. Mol. Biol.* 254, pp. 392-403 (1995).

* cited by examiner

*Primary Examiner* — Maher M Haddad
(74) *Attorney, Agent, or Firm* — Leydig, Voit & Mayer, Ltd.

(57) ABSTRACT

An Ang2 specific antibody, a method of inhibiting angiogenesis or a method of treating a disease related to the activation and/or overproduction of Ang2 using the antibody, and a composition for diagnosing a disease related to the activation and/or overproduction of Ang2 including the antibody.

6 Claims, 3 Drawing Sheets

ANGIOPOIETIN-2 SPECIFIC ANTIBODIES AND USES THEREOF

CROSS-REFERENCE TO RELATED APPLICATIONS

This application claims the benefit of Korean Patent Application No. 10-2013-0090209 filed on Jul. 30, 2013 in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 49,586 bytes ASCII (Text) file named "718051_ST25.TXT," created Jul. 30, 2014.

BACKGROUND

1. Field

Provided is an antibody specifically binding to an angiogenesis-inducing factor Ang2 to inhibit the function thereof. In particular, provided are an Ang2 specific antibody, a method of inhibiting angiogenesis or a method of treating a disease related to the activation and/or overproduction of Ang2 using the antibody, and a composition for diagnosing a disease related to the activation and/or overproduction of Ang2 including the antibody.

2. Description of the Related Art

Angiogenesis refers to a mechanism through which a new blood vessel is formed from a pre-existing blood vessel, and has been known to play an important role in the formation of an organ, normal physiological growth, wound healing and so on. Also, abnormal angiogenesis has been known to play a crucial role in diseases such as tumor growth and metastasis, age-related macular degeneration, diabetic retinopathy, psoriasis, rheumatoid arthritis, and chronic inflammation Angiogenesis has been known to play an important role in tumor growth and metastasis, and various intensive researches on angiogenesis mechanism for developing a new cancer drug have been going on by developed countries and multinational pharmaceutical companies. One of the proteins that has been the target of research is Angiopoietin which has been known to be involved in blood vessel development and angiogenesis after birth, and known are Ang-1, 2, 3 and 4.

Angiogenesis related to Angiopoietin-2 (Ang2) in a cancer tissue is believed to occur as follows. First, for angiogenesis in the cancer tissue, cooption wherein cancer cells select pre-existing blood vessels to form new blood vessels in a cancer tissue occurs. Thereafter, blood vessel regression during which the functions of the pre-existing blood vessels are destroyed by Ang2 pathway occurs. The regression of the pre-existing vessels causes hypoxic environment within the cancer tissue, which is an environment where the formation of new blood vessels is possible. Under such conditions, the expression of vascular endothelial cell growth factor (VEGF) is increased, and new blood vessels are thus formed. For such a reason, Ang2 is an important target in the development of angiogenesis inhibitors, and various kinds of angiogenesis inhibitors are currently being developed and actively undergoing preclinical or clinical trials.

Under such a circumstance that Ang2 is of increasing importance as a target for developing an angiogenesis inhibitor, there is a need of developing an effective and strong Ang2 target substance.

SUMMARY

One embodiment provides an anti-Ang2 antibody or an antigen-binding fragment thereof, which specifically binds to Ang2.

Another embodiment provides a pharmaceutical composition including the anti-Ang2 antibody or an antigen-binding fragment thereof as an active ingredient. The composition may be used for inhibiting angiogenesis or preventing and/or treating a disease related to activation or overproduction (overexpression) of Ang2.

Another embodiment provides a method of inhibiting angiogenesis, including administering to a subject the anti-Ang2 antibody or an antigen-binding fragment thereof.

Another embodiment provides a method of preventing and/or treating a disease related to activation or overproduction (e.g., overexpression) of Ang2, including administering the anti-Ang2 antibody or an antigen-binding fragment thereof to a subject.

Another embodiment provides a method for screening a candidate substance for diagnosing, preventing or treating a disease related to activation or overproduction (overexpression) of Ang2, using one or more binding regions on Ang2 for the anti-Ang2 antibody or an antigen-binding fragment thereof.

Still another embodiment provides a novel polypeptide capable of having a function as an antigen binding site of an anti-Ang2 antibody or an antigen-binding fragment thereof.

DETAILED DESCRIPTION

Figure 1:
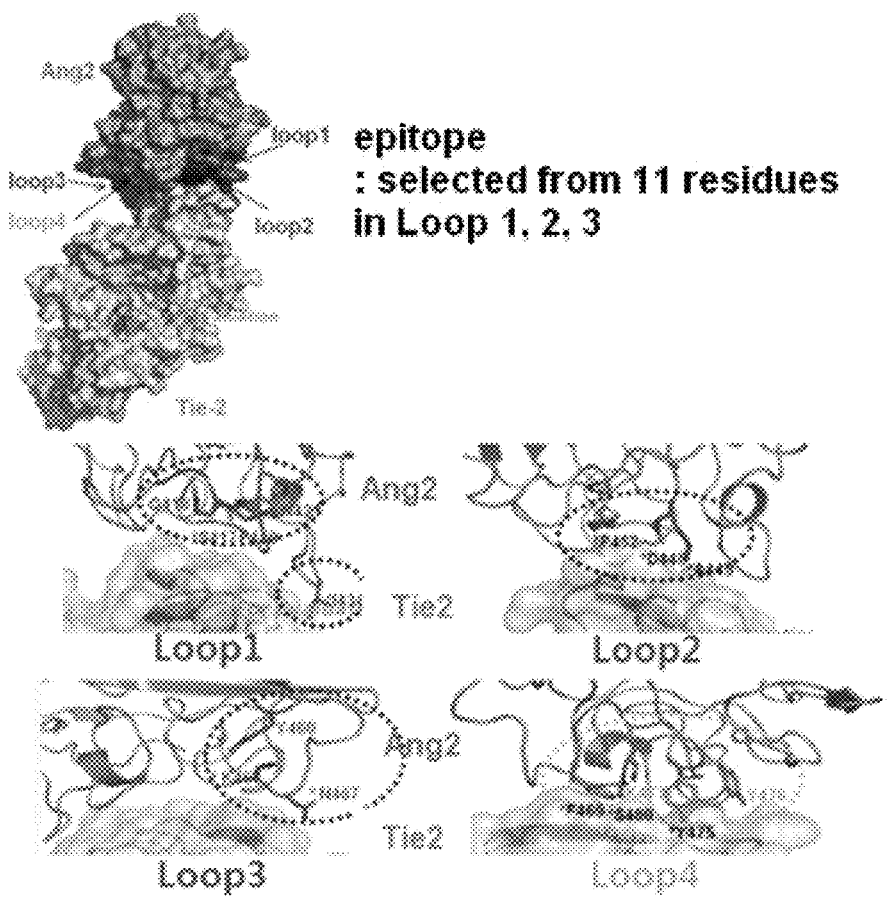
FIG. 1 is a schematic diagram showing binding between an anti-Ang2 antibody and an epitope on Ang2.

Provided in the present disclosure is an antibody that inhibits the functions of an angiogenesis-inducing factor angiopoietin-2 (Ang2). Also provided is an antibody (or antigen binding fragment thereof) useful for diagnosing and treating a disease associated with the activation and/or overproduction (overexpression) of Ang2 and suppressing angiogenesis in a cancer tissue by hindering Ang2, a factor inducing angiogenesis which is essential for the growth of cancer cells in the cancer tissue, from binding to its intracellular receptor, Tie2 receptor.

In addition to the effect of inhibiting the binding between Ang2 and Tie2 receptor, provided is an anti-Ang2 antibody which provides enhanced cancer cell growth inhibition and/or cancer metastasis inhibitory effect by inhibiting binding between Ang2 and other proteins involved in the growth of cancer cells and/or cancer metastasis, for example, integrin, and can exhibit such an effect even in a cell which does not express Tie2.

Ang2 protein is closely related to angiogenesis. It is a soluble ligand present in blood, and it is a therapeutic target protein which attracts the attention of drug developers. Human Ang2 protein is thought to be widely involved in angiogenesis, metastasis, cancer cell invasion, etc. such that suppression of binding to its receptor, Tie2 receptor, using an antibody to suppress angiogenesis, cancer incidence, and cancer cell metastasis, wherein the antibody can be used for diagnosis and/or treatment of a disease associated with the activation and/or overproduction (overexpression) of Ang2.

The term "antibody" as used in the present disclosure includes any animal antibodies, chimeric antibodies, humanized antibodies or fully human antibodies. Furthermore, the antibody in the disclosure also includes antigen-binding fragments of an antibody which possess an antigen binding potential. Meanwhile, complementarity-determining regions (CDRs) in the disclosure refer to regions within the variable region of an antibody or antibody fragment which contribute specificity for antigen binding. The antigen-binding fragments of an antibody may be antibody fragments including at least one complementarity-determining region.

In connection with angiogenesis process in a cancer tissue, cooption wherein cancer cells select pre-existing blood vessels to form new blood vessels in a cancer tissue occurs. Thereafter, blood vessel regression during which the functions of the pre-existing blood vessels are destroyed by Ang2 pathway occurs. The regression of the pre-existing vessels causes a hypoxic environment within the cancer tissue, which is an environment where the formation of new blood vessels is possible. Under such conditions, the expression of vascular endothelial cell growth factor (VEGF) is increased, and new blood vessels are thus formed. As Angiopoietin proteins, Ang1, Ang2, Ang3, and Ang4, have been known and of them, Ang2 is also known as ANGPT2 and is expressed in blood vessel remodeling areas.

Ang2, which becomes a target of an antibody to be provided in one embodiment, is closely related to angiogenesis, it is a soluble ligand present in blood, and it is widely involved in angiogenesis, metastasis, and cancer cell invasion. The Ang2 may be derived (originated) from mammals including primates such as humans and monkeys and rodents such as rats and mice and for example, it may be selected from the group consisting of a human Ang2 (e.g., NCBI Accession #O15123), a monkey Ang2 (e.g., NCBI Accession No. Q8MIK6 etc.), a mouse Ang2 (NCBI Accession #NP_031452, Accession #O35608, etc.), a rat Ang2 (e.g., NCBI Accession No. O35462, etc.), and any combination thereof.

Lately, antibodies have been widely used for treating diseases. As antibodies are very stable in vivo as well as in vitro and have a long half-life, they are favorable for mass expression and production. Also, since an antibody has intrinsically a dimer structure, it has a fairly high avidity. In one embodiment of the disclosure, the antibody has binding activity to Ang2 and it is an antibody having the effect of suppressing angiogenesis in a cancer tissue by hindering Ang2 from binding to its intracellular receptor, Tie2 receptor. Specifically, the antibody according to one embodiment may inhibit binding between Ang2 and Tie2 receptor by competing with Tie2 to bind to Ang2 and for example, it may inhibit binding between Ang2 and Tie2 receptor by recognizing and/or binding to a binding site of Ang2 for binding to Tie2 receptor.

Furthermore, the antibody may further have activity of inhibiting binding between Ang2 and integrin (see Example 10). The integrin is a typical protein which mediates cell adhesion and has a heterodimer structure including an alpha ($\alpha$) subunit and a beta ($\beta$) subunit. In mammals, 18 types of alpha subunits and 8 types of beta subunits have been identified. The integrin may be derived from mammals including primates such as humans and monkeys and rodents such as mice and rats and for example, it may be a human integrin, a monkey integrin, a mouse integrin and a rat integrin, but is not limited thereto. In each and every species, 24 types of integrins have been known and amino acid sequences thereof have been well identified so that they are clear matters to those who have ordinary knowledge in the art to which the invention pertains. For example, the integrin may be a human integrin and typical human integrin types may include, but not limited to, alpha5beta1 ($\alpha5\beta1$) ($\alpha5$: NCBI Accession No. P08648, $\beta1$: NCBI Accession No. P05556), alphaVbeta1 ($\alpha V\beta1$) ($\alpha V$: NCBI Accession No. P06756, $\beta1$: NCBI Accession No. P05556), and alphaVbeta3 ($\alpha V\beta3$) ($\alpha V$: NCBI Accession No. P06756, $\beta3$: NCBI Accession No. P05106).

In an embodiment of the disclosure, an anti-Ang2 antibody or an antigen-binding fragment thereof is provided. The anti-Ang2 antibody may recognize (specifically bind) all or part (for example, at least one amino acid residue exposed to the outside of each loop) of the regions consisting of loop 1 (a region covering from $417^{th}$ to $434^{th}$ amino acids of SEQ ID NO: 70), loop 2 (a region covering from $447^{th}$ to $454^{th}$ amino acids of SEQ ID NO: 70), and loop 3 (a region covering from $460^{th}$ to $468^{th}$ amino acids of SEQ ID NO: 70) of human Ang2 (hAng2; SEQ ID NO: 70; Accession #O15123). The anti-Ang2 antibody may recognize (specifically bind) an amino acid sequence region including 2 to 20, 2 to 15, 2 to 10, or 2 to 5 contiguous amino acids of SEQ ID NO: 70, including at least one amino acid residue exposed to the outside of loop 1, loop 2, or loop 3 of SEQ ID NO: 70 as an epitope.

For example, the anti-Ang2 antibody may recognize (specifically bind) at least one amino acid residue selected from the group consisting of I434 positioned at loop 1, A449 and P452 positioned at loop 2, and N467 positioned at loop 3 of human Ang2, or an amino acid sequence region including 2 to 20, 2 to 15, 2 to 10, or 2 to 5 contiguous amino acids including the above at least one amino acid residue as an epitope. In one embodiment, the anti-Ang2 antibody may recognize at least one amino acid residue selected from the group consisting of I434 positioned at loop 1, A449 and P452 positioned at loop 2, and N467 positioned at loop 3 of human Ang2 as an epitope, or specifically bind to this portion.

[Ang2 (SEQ ID NO: 70; loop 1, loop 2 and loop 3 are underlined respectively in order and each epitope is marked in bold letters)]

```
MWQIVFFTLS CDLVLAAAYN NFRKSMDSIG KKQYQVQHGS

CSYTFLLPEM DNCRSSSSPY VSNAVQRDAP LEYDDSVQRL

QVLENIMENN TQWLMKLENY IQDNMKKEMV EIQQNAVQNQ

TAVMIEIGTN LLNQTAEQTR KLTDVEAQVL NQTTRLELQL

LEHSLSTNKL EKQILDQTSE INKLQDKNSF LEKKVLAMED

KHIIQLQSIK EEKDQLQVLV SKQNSIIEEL EKKIVTATVN

NSVLQKQQHD LMETVNNLLT MMSTSNSAKD PTVAKEEQIS

FRDCAEVFKS GHTTNGIYTL TFPNSTEEIK AYCDMEAGGG

GWTIIQRRED GSVDFQRTWK EYKVGFGNPS GEYWLGNEFV

SQLTNQQRYV LKIHLKDWEG NEAYSLYEHF YLSSEELNYR
```

```
       IHLKGLTGTA GKISSISQPG NDFSTKDGDN DKCICKCSQM

LTGGWWFDAC GPSNLNGMYY PQRQNTNKFN GIKWYYWKGS

GYSLKATTMM IRPADF
```

The above epitope sites are exposed amino acid residues positioned at loop 1, loop 2, or loop 3 of the three dimensional structure of Ang2, and they directly participate in binding with a Tie2 receptor or they are positioned by being included in the binding site with the Tie2 receptor or neighboring thereupon (see FIG. 1). Accordingly, the anti-Ang2 antibody or an antigen-binding fragment thereof recognizing and binding to at least one of these epitopes competes with the Tie2 receptor to bind to Ang2 and thus, inhibits binding between Ang2 and the Tie2 receptor.

The term "contiguous amino acid" may include amino acids which are adjacent to one another on the secondary or tertiary structure of a protein as well as amino acids which are continuous on their primary amino acid sequences. Accordingly, the "contiguous amino acid residues" as used herein may refer to consecutive amino acid residues on the primary, secondary, or tertiary structure of a protein.

As not only an anti-Ang2 antibody recognizing and/or specifically binding to the epitope sites, but also an antibody or an antigen-binding fragment thereof which competes with the anti-Ang2 antibody for binding can compete with the Tie2 receptor to bind to Ang2, it can inhibit binding between Ang2 and the Tie2 receptor. This competitively-binding antibody may be an antibody recognizing a site adjacent to the aforementioned epitopes on its three dimensional structure as an epitope. The competitively-binding antibody may have a binding affinity (Kd) of 0.001 to 10 nM, particularly 0.01 to 1 nM, and more particularly 0.07 to 0.8 nM, to Ang2.

Therefore, the anti-Ang2 antibody or an antigen-binding fragment thereof of the invention may be at least one selected from the group consisting of an antibody or an antigen-binding fragment thereof recognizing and/or specifically binding to the aforementioned epitope, and an antibody competing therewith for binding to Ang2 or an antigen-binding fragment thereof.

In an embodiment, the anti-Ang2 antibody or an antigen-binding fragment thereof may comprise a heavy chain complementarity determining region (CDR) comprising at least one selected from the group consisting of a polypeptide (CDR-H1) comprising the amino acid sequence of SEQ ID NO: 49, a polypeptide (CDR-H2) comprising the amino acid sequence of SEQ ID NO: 50, and a polypeptide (CDR-H3) comprising an amino acid sequence selected from the group consisting of SEQ ID NOs: 17 to 24, for example, an amino acid sequence selected from the group consisting of SEQ ID NOs: 17 to 22:

$$X_1\text{-}Y\text{-}X_2\text{-}M\text{-}S \qquad (\text{SEQ ID NO: 49})$$

wherein,
$X_1$ is aspartic acid (D), serine (S), or asparagine (N), for example, aspartic acid (D) or asparagine (N), and
$X_2$ is alanine (A), aspartic acid (D), or tyrosine (Y); and $$X_3\text{-}I\text{-}X_4\text{-}X_5\text{-}X_6\text{-}X_7\text{-}X_8\text{-}X_9\text{-}X_{10}\text{-}Y\text{-}Y\text{-}A\text{-}D\text{-}S\text{-}V\text{-}K\text{-}G \qquad (\text{SEQ ID NO: 50})$$

wherein,
$X_3$ is alanine (A), glycine (G), leucine (L), or serine (S), for example, alanine (A), glycine (G), or serine (S),
$X_4$ is tyrosine (Y) or serine (S),
$X_5$ is proline (P), histidine (H), or serine (S),
$X_6$ is aspartic acid (D), glycine (G), or serine (S),
$X_7$ is serine (S), glycine (G), or aspartic acid (D),
$X_8$ is glycine (G) or serine (S),
$X_9$ is asparagine (N) or serine (S), and
$X_{10}$ is lysine (K), isoleucine (I), or threonine (T).

The anti-Ang2 antibody or an antigen-binding fragment thereof may comprise a light chain complementarity determining region (CDR) comprising at least one selected from the group consisting of a polypeptide (CDR-L1) comprising the amino acid sequence of SEQ ID NO: 51, a polypeptide (CDR-L2) comprising the amino acid sequence of SEQ ID NO: 52, and a polypeptide (CDR-L3) comprising the amino acid sequence of SEQ ID NO: 53:

$$X_{11}\text{-}G\text{-}S\text{-}S\text{-}S\text{-}N\text{-}I\text{-}G\text{-}X_{12}\text{-}N\text{-}X_{13}\text{-}V\text{-}X_{14} \qquad (\text{SEQ ID NO: 51})$$

wherein,
$X_{11}$ is serine (S) or threonine (T),
$X_{12}$ is asparagine (N) or serine (S),
$X_{13}$ is alanine (A), tyrosine (Y), or aspartic acid (D), and
$X_{14}$ is asparagine (N), serine (S), threonine (T), or tyrosine (Y);

$$X_{15}\text{-}X_{16}\text{-}X_{17}\text{-}X_{18}\text{-}R\text{-}P\text{-}S \qquad (\text{SEQ ID NO: 52})$$

wherein,
$X_{15}$ is alanine (A) or serine (S),
$X_{16}$ is aspartic acid (D) or asparagine (N),
$X_{17}$ is serine (S) or asparagine (N), for example serine (S), and
$X_{18}$ is asparagine (N), Lysine (K), histidine (H), or glutamine (Q); and $$X_{19}\text{-}X_{20}\text{-}W\text{-}D\text{-}X_{21}\text{-}S\text{-}L\text{-}X_{22}\text{-}X_{23} \qquad (\text{SEQ ID NO: 53})$$

wherein,
$X_{19}$ is glycine (G) or alanine (A),
$X_{20}$ is serine (S), alanine (A), or threonine (T), for example serine (S) or threonine (T),
$X_{21}$ is tyrosine (Y), or aspartic acid (D), for example, tyrosine (Y),
$X_{22}$ is serine (S) or asparagine (N), for example, serine (S), and
$X_{23}$ is glycine (G) or alanine (A).

In a specific embodiment, the anti-Ang2 antibody or an antigen-binding fragment thereof may comprise or consist essentially of the above heavy chain complementarity determining region, light chain complementarity determining region, or combination thereof.

More particularly, the anti-Ang2 antibody or an antigen-binding fragment thereof may comprise or consist essentially of:

at least one heavy chain complementarity determining region selected from the group consisting of a polypeptide (CDR-H1) comprising the amino acid sequence of SEQ ID NO: 49, a polypeptide (CDR-H2) comprising the amino acid sequence of SEQ ID NO: 50, and a polypeptide (CDR-H3) comprising an amino acid sequence selected from the group consisting of SEQ ID NOs: 17 to 24, for example, an amino acid sequence selected from the group consisting of SEQ ID NOs: 17 to 22, or a heavy chain variable region including the at least one heavy chain complementarity determining region;

at least one light chain complementarity determining region selected from the group consisting of a polypeptide (CDR-L1) comprising the amino acid sequence of SEQ ID NO: 51, a polypeptide (CDR-L2) comprising the amino acid sequence of SEQ ID NO: 52, and a polypeptide (CDR-L3) comprising the amino acid sequence of SEQ ID NO: 53, or a light chain variable region including the at least one light chain complementarity determining region;

a combination of the at least one heavy chain complementarity determining region and the at least one light chain complementarity determining region; or a combination of the heavy chain variable region and the light chain variable region.

Specifically, the heavy chain CDR of the anti-Ang2 antibody may have amino acid sequences, for example, as set forth in the following Table 1.

TABLE 1

Amino acid sequence of heavy chain CDR

| CDRH1-KABAT | CDRH2-KABAT | CDRH3-KABAT |
|---|---|---|
| DYAMS (SEQ ID NO: 1) | AIYPDSGNKYYADSVKG (SEQ ID NO: 9) | ARHSSDPKVKSGYYDDGMDV (SEQ ID NO: 17) |
| DYYMS (SEQ ID NO: 2) | GIYPSGGSTYYADSVKG (SEQ ID NO: 10) | ARDPSTLTYAGFDY (SEQ ID NO: 18) |
| NYAMS (SEQ ID NO: 3) | AISSGGGNIYYADSVKG (SEQ ID NO: 11) | AKSGIQPSPPSMSSAYAMDV (SEQ ID NO: 19) |
| DYAMS (SEQ ID NO: 4) | SIYPDDGNTYYADSVKG (SEQ ID NO: 12) | ARHTSHHTSIDGYYYYGMDG (SEQ ID NO: 20) |
| DYDMS (SEQ ID NO: 5) | SISHGDSNKYYADSVKG (SEQ ID NO: 13) | AKSSGIQESPPTYYYYGMDV (SEQ ID NO: 21) |
| DYAMS (SEQ ID NO: 6) | SIYPDDGNTYYADSVKG (SEQ ID NO: 14) | AKHPVRLNLHPMYYYYGMDV (SEQ ID NO: 22) |
| SYDMS (SEQ ID NO: 7) | LISPDSSSIYYADSVKG (SEQ ID NO: 15) | AKDLISFWRGGFDY (SEQ ID NO: 23) |
| DYDMS (SEQ ID NO: 8) | GISSDDGNTYYADSVKG (SEQ ID NO: 16) | ARPTIDKYTLRGYYSYGMDV (SEQ ID NO: 24) |

Likewise, the light chain CDR of the anti-Ang2 antibody may have amino acid sequences, for example, as set forth in the following Table 2.

TABLE 2

Amino acid sequence of light chain CDR

| CDRL1-KABAT | CDRL2-KABAT | CDRL3-KABAT |
|---|---|---|
| SGSSSNIGNNAVN (SEQ ID NO: 25) | ADSNRPS (SEQ ID NO: 33) | GSWDYSLSG (SEQ ID NO: 41) |
| SGSSSNIGNNYVT (SEQ ID NO: 26) | ADSHRPS (SEQ ID NO: 34) | ATWDYSLSG (SEQ ID NO: 42) |
| SGSSSNIGNNDVY (SEQ ID NO: 27) | ANSHRPS (SEQ ID NO: 35) | GTWDYSLSG (SEQ ID NO: 43) |
| TGSSSNIGNNDVS (SEQ ID NO: 28) | SDSKRPS (SEQ ID NO: 36) | GSWDYSLSG (SEQ ID NO: 44) |

TABLE 2-continued

Amino acid sequence of light chain CDR

| CDRL1-KABAT | CDRL2-KABAT | CDRL3-KABAT |
|---|---|---|
| SGSSSNIGSNAVN (SEQ ID NO: 29) | ADSNRPS (SEQ ID NO: 37) | GSWDYSLSG (SEQ ID NO: 45) |
| TGSSSNIGNNAVS (SEQ ID NO: 30) | SDSQRPS (SEQ ID NO: 38) | ATWDYSLSA (SEQ ID NO: 46) |
| SGSSSNIGSNYVN (SEQ ID NO: 31) | SDSHRPS (SEQ ID NO: 39) | GAWDDSLSG (SEQ ID NO: 47) |
| TGSSSNIGSNYVS (SEQ ID NO: 32) | SDNKRPS (SEQ ID NO: 40) | GTWDDSLNG (SEQ ID NO: 48) |

Particularly, the anti-Ang2 antibody or an antigen-binding fragment thereof may comprise or consist essentially of:

at least one heavy chain complementarity determining region selected from the group consisting of a polypeptide (CDR-H1) comprising an amino acid sequence selected from SEQ ID NOs: 1 to 8, for example, an amino acid sequence selected from SEQ ID NOs: 1 to 6, a polypeptide (CDR-H2) comprising an amino acid sequence selected from SEQ ID NOs: 9 to 16, for example, an amino acid sequence selected from SEQ ID NOs: 9 to 14, and a polypeptide (CDR-H3) comprising an amino acid sequence selected from the group consisting of SEQ ID NOs: 17 to 24, for example, an amino acid sequence selected from SEQ ID NOs: 17 to 22, or a heavy chain variable region including the at least one heavy chain complementarity determining region;

at least one light chain complementarity determining region selected from the group consisting of a polypeptide (CDR-L1) comprising an amino acid sequence selected from SEQ ID NOs: 25 to 32, for example, an amino acid sequence selected from SEQ ID NOs: 25 to 30, a polypeptide (CDR-L2) comprising an amino acid sequence selected from SEQ ID NOs: 33 to 40, for example, an amino acid sequence selected from SEQ ID NOs: 33 to 38, and a polypeptide (CDR-L3) comprising an amino acid sequence selected from SEQ ID NOs: 41 to 48, for example, an amino acid sequence selected from SEQ ID NOs: 41 to 46, or a light chain variable region including the at least one light chain complementarity determining region;

a combination of the at least one heavy chain complementarity determining region and the at least one light chain complementarity determining region; or a combination of the heavy chain variable region and the light chain variable region.

In one embodiment, the heavy chain variable region may include an amino acid sequence selected from the group consisting of SEQ ID NOs: 54 to 61, for example, an amino acid sequence selected from the group consisting of SEQ ID NOs: 54 to 59, and the light chain variable region may include an amino acid sequence selected from the group consisting of SEQ ID NOs: 62 to 69, for example, an amino acid sequence selected from the group consisting of SEQ ID NOs: 62 to 67. Accordingly, the anti-Ang2 antibody or an antigen-binding fragment thereof may include a heavy chain variable region including an amino acid sequence selected from the group consisting of SEQ ID NOs: 54 to 61, for example, an amino acid sequence selected from the group consisting of SEQ ID NOs: 54 to 59; a light chain variable region including an amino acid sequence selected from the group consisting of SEQ ID NOs: 62 to 69, for example, an amino acid sequence selected from the group consisting of SEQ ID NOs: 62 to 67; or a combination of the heavy chain variable region and the light chain variable region.

In another embodiment, the anti-Ang2 antibody or an antigen-binding fragment thereof may comprise or consist essentially of:

at least one heavy chain complementarity determining region selected from the group consisting of a polypeptide (CDR-H1) including the amino acid sequence of SEQ ID NO: 7 or 8, a polypeptide (CDR-H2) including the amino acid sequence of SEQ ID NO: 15 or 16, and a polypeptide (CDR-H3) including the amino acid sequence of SEQ ID NO: 23 or 24, or a heavy chain variable region including it;

at least one light chain complementarity determining region selected from the group consisting of a polypeptide (CDR-L1) including the amino acid sequence of SEQ ID NO: 31 or 32, a polypeptide (CDR-L2) including the amino acid sequence of SEQ ID NO: 39 or 40, and a polypeptide (CDR-L3) including the amino acid sequence of SEQ ID NO: 47 or 48, or a light chain variable region including it;

a combination of the at least one heavy chain complementarity determining region and the at least one light chain complementarity determining region; or a combination of the heavy chain variable region and the light chain variable region.

In one embodiment, the heavy chain variable region may include the amino acid sequence of SEQ ID NO: 60 or 61, and the light chain variable region may include the amino acid sequence of SEQ ID NO: 68 or 69. Accordingly, the anti-Ang2 antibody or an antigen-binding fragment thereof may include a heavy chain variable region including the amino acid sequence of SEQ ID NO: 60 or 61; a light chain variable region including the amino acid sequence of SEQ ID NO: 68 or 69; or a combination of the heavy chain variable region and the light chain variable region.

An animal-derived antibody which is produced by immunizing an animal with a desired antigen may generally trigger an immune rejection response when administered to humans for treatment purpose, and a chimeric antibody has been developed to suppress such immune rejection response. A chimeric antibody is formed by replacing the constant region of an animal-derived antibody, which is a cause of anti-isotype response, with the constant region of a human antibody using genetic engineering methods. The chimeric antibody has considerably improved anti-isotype response in comparison with animal-derived antibodies, but animal-derived amino acids are still present in its variable regions and thus it still contains potential side effects resulting from an anti-idiotypic response. It is a humanized antibody that has been thus developed to improve such side effects. This is manufactured by grafting CDR (complementarity determining regions) which, of the variable regions of a chimeric antibody, has an important role in antigen binding into a human antibody framework.

In CDR grafting technology for manufacturing a humanized antibody, it is important to select an optimized human antibody which can accommodate the CDR of an animal-derived antibody and for this, utilization of antibody database, analysis of crystal structure, molecule modeling technology, etc. are employed. However, although the CDR of an animal-derived antibody is grafted into an optimized human antibody framework, there are a considerable number of cases where antigen binding affinity is not preserved because there are amino acids which affect antigen binding while being positioned at the framework of the animal-derived antibody. In this regard, it may be essential to apply an additional antibody engineering technology for restoring antigen binding affinity.

According to one embodiment, the antibody may be a mouse-derived antibody, a mouse-human chimeric antibody, a humanized antibody, or a human antibody. The antibody or an antigen-binding fragment thereof may be isolated from a living body or non-naturally occurring. The antibody or an antigen-binding fragment thereof may be synthetic or recombinant.

An intact antibody has a structure with two full-length light chains and two full-length heavy chains, and each light chain is linked to each heavy chain via a disulfide bond. The constant region of an antibody is divided into a heavy chain constant region and a light chain constant region, and the heavy chain constant region has gamma (γ), mu (μ), alpha (α), delta (δ) and epsilon (ε) types, and has gamma1 (γ1), gamma2 (γ2), gamma3 (γ3), gamma4 (γ4), alpha1 (α1) and alpha2 (α2) as its subclass. The light chain constant region has kappa (κ) and lambda (λ) types.

The term "heavy chain" is understood to include a full-length heavy chain and fragments thereof, the full-length heavy chain including a variable region domain $V_H$ including an amino acid sequence having sufficient variable region sequences that contribute the specificity for antigen binding and three constant region domains $C_{H1}$, $C_{H2}$ and $C_{H3}$ domains and a hinge. The term "light chain" is understood to include a full-length light chain and fragments thereof, the full-length light chain including a variable region domain $V_L$ including an amino acid sequence having sufficient variable region sequences that contribute to the specificity for antigen binding and a constant region domain $C_L$.

The term "CDR (complementarity determining region)" refers to an amino acid sequence found in the hypervariable region of a heavy chain and a light chain of an immunoglobulin. The heavy and light chain may each include three CDRs (CDRH1, CDRH2, CDRH3, and CDRL1, CDRL2, CDRL3). The CDRs of an antibody can provide an essential contact residue for binding to an antigen or an epitope. Throughout the specification, the terms "specifically binding" or "specifically recognizing" has the same meaning as generally known to an ordinary person in the art, indicating that an antigen and an antibody specifically interact with each other to lead to an immunological response.

The rest region except the aforementioned CDR regions or light chain variable regions and heavy chain variable regions of the anti-Ang2 antibody, e.g., a light chain constant region and a heavy chain constant region, may be originated from any subtypes of an immunoglobulin (e.g., IgA, IgD, IgE, IgG (e.g., IgG1, IgG2, IgG 3, and IgG4), IgM, etc), for example, a light chain constant regions and heavy chain constant regions of IgA, IgD, IgE, IgG (e.g., IgG1, IgG2, IgG 3, and IgG4), IgM, etc.

According to one embodiment, the antibody may be an antigen-binding fragment selected from the group consisting of an scFv, an (scFv)$_2$, an scFv-Fc, an Fab, an Fab' and an F(ab')$_2$.

The term "antigen-binding fragment," which is a fragment of the full structure of an immunoglobulin, refers to some of a polypeptide including a portion to which an antigen can bind. For example, it may be an scFv, an (scFv)$_2$, an Fab, an Fab', or an F(ab')$_2$, but is not limited thereto. Among the antigen-binding fragments, a Fab, which is a structure having the light chain and heavy chain variable regions, the light chain constant region, and the heavy chain first constant region ($C_{H1}$), has one antigen binding site.

An Fab' differs from the Fab in that the Fab' has a hinge region including at least one cysteine residue at the C-terminal of the heavy chain $C_{H1}$ domain.

An F(ab')$_2$ antibody is produced when cysteine residues at the hinge region of the Fab' are joined by a disulfide bond. An Fv is a minimal antibody fragment, having only heavy chain variable regions and light chain variable regions, and a recombinant technique for producing the Fv fragment is well known in the art.

A two-chain Fv may have a structure in which heavy chain variable regions are linked to light chain variable regions by a non-covalent bond, and a single-chain Fv may generally form a dimer structure as in the two-chain Fv, wherein heavy chain variable regions are covalently bound to light chain variable regions via a peptide linker or the heavy and light chain variable regions are directly linked to each other at the C-terminals thereof. The peptide linker may include 1 to 100 or 2 to 50 any amino acids, and proper sequences thereof have been known in the art.

The antigen-binding fragment may be obtained using a protease (for example, a whole antibody can be digested with papain to obtain Fab fragments, or can be digested with pepsin to obtain F(ab')$_2$ fragments), or may be prepared by a genetic recombinant technique.

The term "hinge region" refers to a region included in the heavy chains of an antibody, which is present between the CH1 and CH2 regions, and provides flexibility to the antigen binding site in the antibody.

When an animal-derived antibody goes through a chimerization process, an animal-derived IgG1 hinge is replaced with a human IgG1 hinge, but a length of the animal-derived IgG1 hinge is shorter than the human IgG1 hinge, and disulfide bonds between two heavy chains are reduced from 3 to 2. Thus, rigidity of the hinges may have different effects. Therefore, modification of a hinge region can increase an antigen binding efficiency of a humanized antibody. Methods of deleting, inserting, or substituting an amino acid for modifying amino acid sequences of the hinge region are well known in the art.

The anti-Ang2 antibody may be a monoclonal antibody. The monoclonal antibody may be prepared by methods well known in the art. For example, it may be prepared using a phage display technique.

Meanwhile, individual monoclonal antibodies may be screened using a typical ELISA (Enzyme-Linked ImmunoSorbent Assay) format, based on the binding potential with Ang2. Inhibitory activities can be verified through functional analysis such as competitive ELISA for verifying the molecular interaction of binding assemblies or functional analysis such as a cell-based assay. Then, with regard to monoclonal antibody members selected on the basis of their strong inhibitory activities, their affinities (Kd values) to Ang2 may be each verified.

Another embodiment provides a pharmaceutical composition including the anti-Ang2 antibody or an antigen-binding fragment thereof.

In particular, another embodiment provides a pharmaceutical composition for inhibiting angiogenesis, including the anti-Ang2 antibody or an antigen-binding fragment thereof as an active ingredient. Still another embodiment provides a pharmaceutical composition for preventing and/or treating a disease related to the activation and/or overproduction (overexpression) of Ang2, including the anti-Ang2 antibody or an antigen-binding fragment thereof as an active ingredient.

In another embodiment, there is provided a method for inhibiting angiogenesis, including administering a pharmaceutically effective amount of the anti-Ang2 antibody or an antigen-binding fragment thereof to a subject. The subject may be in need of the inhibition of angiogenesis. The angiogenesis inhibitory method may further include a step of identifying a subject who is in need of the inhibition of angiogenesis, prior to the administration step. In another embodiment, there is provided a method for preventing and/or treating a disease related to the activation and/or overproduction (overexpression) of Ang2, including administering a pharmaceutically effective amount of the anti-Ang2 antibody or an antigen-binding fragment thereof to a subject. The subject may be in need of the prevention and/or treatment of the disease related to the activation and/or overproduction (overexpression) of Ang2. The prevention and/or treatment method may further include a step of identifying a subject who is in need of the prevention and/or treatment of a disease related to the activation and/or overproduction (overexpression) of Ang2, prior to the administration step.

In another embodiment, there is provided a use of the anti-Ang2 antibody or an antigen-binding fragment thereof for inhibiting angiogenesis, or a use thereof for preparing an angiogenesis inhibitor. In another embodiment, there is provided a use of the anti-Ang2 antibody or an antigen-binding fragment thereof for preventing and/or treating a disease related to the activation and/or overproduction (overexpression) of Ang2, or a use thereof for preparing a drug for the prevention and/or treatment of the disease.

The pharmaceutical composition may further include a pharmaceutically acceptable carrier, and the carrier may be those commonly used in the formulation of drugs, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but is not limited thereto. The pharmaceutical composition may further include one or more selected from the group consisting of a diluent, an excipient, a lubricant, a wetting agent, a sweetener, a flavor enhancer, an emulsifying agent, a suspension agent, and a preservative.

The pharmaceutical composition may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the composition may be administered using an optional device that enables an active substance to be delivered to target cells.

The content of the anti-Ang2 antibody or an antigen-binding fragment thereof in the pharmaceutical composition may be prescribed in a variety of ways, depending on factors such as formulation methods, administration methods, age of subjects, body weight, gender, pathologic conditions, diets, administration time, administration interval, administration route, excretion speed, and reaction sensitivity. For example, a daily dosage of the anti-Ang2 antibody or an antigen-binding fragment thereof may be within the range of 0.001 to 1000 mg/kg, particularly 0.01 to 100 mg/kg, and more particularly 0.1 to 50 mg/kg, but is not limited thereto. The daily dosage may be formulated into a single formulation in a unit dosage form or formulated in suitably divided dosage forms, or it may be manufactured to be contained in a multiple dosage container. The term "pharmaceutically effective amount" as used herein refers to a content or dose of an active ingredient capable of showing desirable pharmacological effects and it may be determined in a variety of ways, depending on factors such as formulation methods, administration methods, age of subjects, body weight, gender, pathologic conditions, diets, administration time, administration interval, administration route, excretion speed, and reaction sensitivity.

The pharmaceutical composition may be formulated into a form of a solution in oil or an aqueous medium, a suspension, syrup, an emulsifying solution, an extract, powder, granules, a tablet, or a capsule, and may further include a dispersing or a stabilizing agent for the formulation.

In particular, the pharmaceutical composition including the anti-Ang2 antibody or an antigen-binding fragment thereof may be formulated into an immunoliposome since it contains an antibody or an antigen-binding fragment. A liposome containing an antibody may be prepared using any methods widely known in the art. The immunoliposome may be a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide-exchange reaction.

Meanwhile, as the anti-Ang2 antibody or an antigen-binding fragment thereof specifically binds to Ang2, this can be used for detecting Ang2, or the activation and/or overproduction (overexpression) of Ang2.

Accordingly, another embodiment of the disclosure provides a composition for detecting Ang2, including the anti-Ang2 antibody or the antigen-binding fragment thereof. In another embodiment, there is provided a method for detecting Ang2 including treating a biological sample with the anti-Ang2 antibody or the antigen-binding fragment thereof; and identifying the presence of an antigen-antibody reaction. In this detection method, when the antigen-antibody reaction is detected, it can be determined that Ang2 is present in the biological sample. Another embodiment provides a use of the anti-Ang2 antibody or an antigen-binding fragment thereof for detecting Ang2.

By virtue of such use of the anti-Ang2 antibody or an antigen-binding fragment thereof for detecting Ang2, the activation and/or overproduction (overexpression) of Ang2 can be verified and this can be used to diagnose a disease related to the activation and/or overproduction (overexpression) of Ang2.

Accordingly, another embodiment provides a composition for detecting the activation and/or overproduction (overexpression) of Ang2, or a pharmaceutical composition for diagnosing a disease related to the activation and/or overproduction (overexpression) of Ang2 including the anti-Ang2 antibody or the antigen-binding fragment thereof. Another embodiment provides a method for detecting the activation and/or overproduction (overexpression) of Ang2, or a method for diagnosing a disease related to the activation and/or overproduction (overexpression) of Ang2 or a method of providing information for diagnosis thereof, including treating a biological sample obtained from a subject with the anti-Ang2 antibody or the antigen-binding fragment thereof and identifying the presence of an antigen-antibody reaction. The detection method, the diagnose method, or the method of providing information for diagnosis may further include a step of determining the subject to have Ang2 activation and/or overproduction (overexpression) symptoms or to have a disease related to Ang2 activation and/or overproduction (overexpression) in case that the antigen-antibody reaction is detected, subsequently to the antigen-antibody reaction identification step. Another embodiment provides a use of the anti-Ang2 antibody or an antigen-binding fragment thereof for detecting Ang2 activation and/or overproduction (overexpression) or for diagnosing a disease related to Ang2 activation and/or overproduction (overexpression).

The biological sample may be selected from the group consisting of cells, tissues and body fluids (for example, serum) obtained (isolated) from a subject, and culture thereof.

The step of identifying the presence of the antigen-antibody reaction may be performed using various methods known in the art. For example, it may be measured through an ordinary enzyme reaction, fluorescence, luminescence, and/or radioactivity detection and particularly, it may be measured by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, etc., but is not limited thereto.

The subjects which the pharmaceutical composition is administered to or is aimed to diagnose may be selected from mammals including primates such as humans and monkeys, or rodents such as rats and mice.

The diseases related to the activation and/or overproduction of Ang2 may be cancer; cancer metastasis; cancer invasion/penetration; eye diseases such as macular degeneration (e.g., age-related macular degeneration), diabetic retinopathy, etc.; inflammatory diseases such as psoriasis, rheumatoid arthritis, chronic inflammation, septicemia; malaria, etc. The cancer may be those overexpressing Ang2, it may be a solid cancer or a blood cancer, and it may be, but not limited to, selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatocellular cancer, gastric cancer, pancreatic cancer, glioblastoma, cervical cancer, ovarian cancer, liver cancer, bladder cancer, hepatoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, etc.

In another embodiment, there is provided a method for screening a candidate substance for diagnosing, preventing, and/or treating a disease related to the activation and/or overproduction (overexpression) of Ang2 using the above epitope. The screening method includes (a) contacting a candidate compound to the three dimensional structure epitope of the aforementioned Ang2; and (b) measuring binding between the epitope and the candidate compound.

In the step of measuring binding, when the epitope and the candidate compound show binding affinity in the range of 0.001 to 10 nM, particularly 0.01 to 1 nM, and more particularly, 0.07 to 0.8 nM, the candidate compound can be determined to be a candidate substance for diagnosing, preventing, and/or treating a disease related to the activation and/or overproduction (overexpression) of Ang2. For example, to ensure proper folding of the protein, the steps may be conducted under the conditions of about 20 to 35° C. (e.g., room temperature) and/or pH 7 to 8 (e.g., pH 7.4).

The step of measuring binding may be carried out using various methods known in the art. For example, it may be measured through an ordinary enzyme reaction, fluorescence, luminescence, and/or radioactivity detection and particularly, it may be measured by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, etc., but is not limited thereto.

The epitope may be all or part (for example, at least one selected from the group consisting of the amino acid residue regions exposed to the outside of each loop) of the regions consisting of loop 1 (a region covering from $417^{th}$ to $434^{th}$ amino acids of SEQ ID NO: 70), loop 2 (a region covering from $447^{th}$ to $454^{th}$ amino acids of SEQ ID NO: 70), and loop 3 (a region covering from $460^{th}$ to $468^{th}$ amino acids of SEQ ID NO: 70) of human Ang2 (hAng2; SEQ ID NO: 70), or an amino acid sequence region including 2 to 20, 2 to 15, 2 to 10, or 2 to 5 continuous or non-continuous amino acids including at least one amino acid residue exposed to the outside of loop 1, loop 2, or loop 3 of SEQ ID NO: 70 and for example, it may be at least one amino acid residue selected from the group consisting of I434 positioned at loop 1, A449 and P452 positioned at loop 2, and N467 positioned at loop 3, or an amino acid sequence region including 2 to 20, 2 to 15, 2 to 10, or 2 to 5 continuous or non-continuous amino acids including the above at least one amino acid residue.

The candidate compounds may be one or more selected from the group consisting of various artificially-synthesized or natural compounds, polypeptides, oligopeptides, polynucleotides, oligonucleotides, antisense-RNA, shRNA (short hairpin RNA), siRNA (small interference RNA), aptamers, natural product extracts and so on.

The step of measuring the binding affinity between the epitope and the candidate compound may be carried out using various methods known in the art. For example, the binding affinity may be measured using Biacore machine. In general, the range within which the binding affinity is considered as a drug for treatment may be defined to have a binding constant KD value of not more than 10 mM. For instance, in case that the binding affinity between the epitope of Ang2 and a candidate compound to be analyzed (for example, antibody) is 0.001 to 10 nM, particularly 0.01 to 1 nM, and more particularly, 0.07 to 0.8 nM when measured using surface plasmon resonance methods such as Biacore machine, the candidate compound (for example, antibody) can be determined to be a candidate substance for diagnosing, preventing, and/or treating a disease related to the activation and/or overproduction (overexpression) of Ang2.

In another embodiment, there is provided a polypeptide molecule including the heavy chain complementarity determining region, the light chain complementarity determining region or the combination thereof or the heavy chain variable region, the light chain variable region or the combination thereof of the anti-Ang2 antibody as described above. The polypeptide molecule may function as a precursor or a component of an antagonist against Ang2 as well as an antibody or an antigen-binding fragment thereof. For example, the polypeptide molecule may function as an Ang2 antigen binding site, and can be included as a component of a protein scaffold (e.g., peptibody, nanobody, etc.), a bispecific antibody, and a multi-specific antibody having a similar structure to an antibody.

The term "antagonist" as used herein is interpreted to encompass all molecules that partially or entirely block, suppress or neutralize at least one biological activity of its target (e.g., Ang2).

The term "peptibody (peptide+antibody)" used herein refers to a fusion protein including a peptide and all or part of the constant region of an antibody such as an Fc portion wherein the peptide serves as an antigen binding site (heavy chain and/or light chain CDR or variable regions) thereby to render a protein having similar framework and functions to an antibody The term "nanobody" used herein is called a single-domain antibody, refers to an antibody fragment including a single variable domain of an antibody as a monomer form, and has characteristics of selectively binding to a specific antigen similarly to an antibody having an intact structure. The molecular weight of the nanobody is generally about 12 kDa to about 15 kDa, which is very little when compared to the normal molecular weight (about 150 kDa or about 160 kDa) of an intact antibody (including two heavy chains and two light chains) and in some cases it is smaller than an Fab fragment or scFv fragment.

The term "bispecific antibody" or "multi-specific antibody" used herein refers to an antibody recognizing and/or binding to two (bispecific antibody) or more (multi-specific antibody) different antigens, or recognizing and/or binding to different sites of the same antigen, and one antigen binding site of the bispecific antibody or multi-specific antibody may include the polypeptide described above.

In a specific embodiment, the polypeptide molecule may include at least one selected from the group consisting of a polypeptide including the amino acid sequence of SEQ ID NO: 49 (for example, an amino acid sequence selected from the group consisting of SEQ ID NO: 1 to SEQ ID NO: 8), a polypeptide including the amino acid sequence of SEQ ID NO: 50 (for example, an amino acid sequence selected from the group consisting of SEQ ID NOs: 9 to 16), and a polypeptide having an amino acid sequence selected from the group consisting of SEQ ID NOs: 17 to 24;

at least one selected from the group consisting of a polypeptide including the amino acid sequence of SEQ ID NO: 51 (for example, an amino acid sequence selected from the group consisting of SEQ ID NO: 25 to SEQ ID NO: 32), a polypeptide including the amino acid sequence of SEQ ID NO: 52 (for example, an amino acid sequence selected from the group consisting of SEQ ID NO: 33 to SEQ ID NO: 40), and a polypeptide including the amino acid sequence of SEQ ID NO: 53 (for example, an amino acid sequence selected from the group consisting of SEQ ID NO: 41 to SEQ ID NO: 48); or a combination thereof.

In a specific embodiment, the polypeptide molecule may include an amino acid sequence selected from the group consisting of SEQ ID NO: 54 to SEQ ID NO: 61; an amino acid sequence selected from the group consisting of SEQ ID NO: 62 to SEQ ID NO: 69; or a combination thereof.

The above bispecific antibody or multi-specific antibody is referred to as an antibody including each antigen binding site to different two or more kinds of antigens and recognizing the two or more kinds of antigens at the same time, wherein one of the antigen binding sites may include the aforementioned polypeptide molecule. In particular, the polypeptide molecule serving as Ang2 antigen binding site may form a dimer or multimer together with an antigen binding site to another antigen to constitute a bi-specific antibody or a multi-specific antibody. Accordingly, in one embodiment, there is provided a bi-specific antibody or a multi-specific antibody including the polypeptide molecule as an Ang2 antigen binding site.

In another embodiment, there is provided a protein scaffold including at least one (e.g., 1 to 5, particularly 2 to 4) peptide complex including one or more of the aforementioned polypeptide molecules or a repeat where the polypeptide molecules are repeatedly linked by a linker (hereafter, 'first peptide') and a polypeptide having a structural function (hereafter, 'second peptide'; e.g., a heavy chain or light chain constant region of an antibody, or an Fc fragment of an antibody) wherein the at least one peptide complex is bound to each other at the second peptide (e.g., Fc fragment) to form a multimer structure.

In another embodiment, there is provided a polynucleotide molecule encoding the polypeptide molecule. Particularly, the polynucleotide molecule may include a nucleotide sequence selected from the group consisting of SEQ ID NO: 71 to SEQ ID NO: 81. In another embodiment, there is provided a recombinant vector including the polynucleotide. In still another embodiment, there is provided a recombinant cell transformed by the recombinant vector. In still another embodiment, provided is a method of preparing the polypeptide molecule including expressing the polynucleotide or the recombinant vector in a suitable host cell.

The term "vector" used herein refers to a means for expressing a target gene in a host cell. For example, the vector may include a plasmid vector, a cosmid vector, and a virus vector, such as a bacteriophage vector, an adenovirus vector, a retrovirus vector, and an adeno-associated virus vector. The recombinant vector may be prepared by manipulating a plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), a phage (for example, λgt4λB, λ-Charon, λΔz1, and M13), or a virus (for example, SV40) often used in the art, but is not limited thereto.

In the recombinant vector, the polynucleotide may be operatively linked to a promoter. The term "operatively linked" used herein means a functional linkage between a nucleotide expression regulating sequence (for example, a promoter sequence) and other nucleotide sequences. Thus, the regulating sequence may regulate the transcription and/or translation of the other nucleotide sequences by being "operatively linked".

The recombinant vector may be typically constructed as a cloning vector or an expression vector. The expression vector may be a vector commonly used in the art for expressing a foreign protein in a plant, animal or microorganism. The recombinant vector may be constructed using various methods known in the art.

The recombinant vector may be constructed for use in prokaryotic or eukaryotic host cells. For example, when a prokaryotic cell is used as a host cell, the expression vector used generally includes a strong promoter capable of initiating transcription (for example, pL$^\lambda$ promoter, CMV promoter, trp promoter, lac promoter, tac promoter, T7 promoter), a ribosome binding site for initiating translation, and a transcription/translation termination sequence. When a eukaryotic cell is used as a host cell, an origin of replication acting in the eukaryotic cell to be included in the vector may include f1 origin of replication, SV40 origin of replication, pMB1 origin of replication, adeno origin of replication, AAV origin of replication, or BBV origin of replication, but is not limited thereto. The promoter in an expression vector for a eukaryotic host cell may be a promoter derived from genomes of mammalian cells (for example, a metallothionein promoter) or a promoter derived from mammalian viruses (for example, an adenovirus late promoter, a vaccinia virus 7.5K promoter, a SV40 promoter, a cytomegalovirus promoter, and a tk promoter of HSV), and the transcription termination sequence may have, in general, a polyadenylation sequence.

The recombinant cell may be obtained by introducing the recombinant vector into a suitable host cell. The host cell, which is capable of stably and consecutively cloning or expressing the recombinant vector, may be any host cells known in the art. The prokaryotic cell may be a *Bacillus* genus bacterial cell, such as *E. coli* JM109, *E. coli* BL21, *E. coli* RR1, *E. coli* LE392, *E. coli* B, *E. coli* X 1776, *E. coli* W3110, *Bacillus subtilis*, and *Bacillus thuringiensis*, intestinal bacteria, such as *Salmonella typhimurium, Serratia marcescens*, and various *Pseudomonas* species. A eukaryotic host cell may be a yeast (*Saccharomyce cerevisiae*), an insect cell, a plant cell, or an animal cell, for example, Sp2/0, CHO (Chinese hamster ovary) K1, CHO DG44, PER.C6, W138, BHK, COS-7, 293, HepG2, Huh7, 3T3, RIN, MDCK cell line and so on, but is not limited thereto.

The polynucleotide or the recombinant vector including the same may be transferred (introduced) into the host cell by using a method widely known in the art. For example, when a prokaryotic cell is used as the host cell, the transfer may be performed using a $CaCl_2$ method or an electroporation method, and when a eukaryotic cell is used as the host cell, the transfer may be performed by microinjection, calcium phosphate precipitation, electroporation, liposome-mediated transfection, or gene bombardment, but is not limited thereto.

The transformed host cell may be selected using a phenotype expressed by a selectable marker by known methods in the art. For example, when the selectable marker is a specific antibiotic resistance gene, a transformant is cultured in a medium containing the antibiotic, and thus the transformant may easily be selected.

The invention intends to provide an anti-Ang2 antibody for target-treating Ang2 which among the factors involved in neovascular formation and growth in a cancer tissue, has been drawing a new attention lately by the elucidation of its molecular mechanism, and it can be usefully developed as a new innovative antibody drug having excellent effects compared to the pre-existing antibody drugs.

Hereafter, the present invention will be described in detail by examples.

The following examples are intended merely to illustrate the invention and are not construed to restrict the invention.

EXAMPLES

Example 1: Preparation of Anti-Ang2 Human Antibody

With regard to human Ang2 polypeptide (R&D systems; Human Ang2; Accession #O15123 (hAng2); SEQ ID NO: 84), a fully human anti-Ang2 antibody was prepared using a phage display scFv library (obtained from Ewha Women's University-Industry Collaboration Foundation). A detailed protocol thereof is as follows:

The Ang2 polypeptide was applied to a Maxisorp immunotube in amounts of about 10 ug (microgram)/ml, 1 ug/ml and 0.1 ug/ml, respectively to enrich antibodies responding to Ang2 through $1^{st}$, $2^{nd}$, and $3^{rd}$ pannings. After the surface of the immunotube was blocked with about 3% (v/v) milk dissolved in PBS, about 1×10$^{12}$ of phage particles derived from the same phage display scFv library as described above were added to about 0.5 ml of 3% (v/v) milk, which was isothermally treated together at 37° C. for 1 hours for blocking After that, the phages blocked with milk were put into the immunotube applied with Ang2, followed by isothermal treatment at a room temperature for 1 hour to allow Ang2 and the phages to be bound.

After the isothermal treatment of the phages, the surface of the phages were washed 3 to 5 times with PBS and about 0.1% (v/v) Tween 20 and then, the bound phages were eluted using 100 mM triethanolamine. The eluted phages were transfected into *E. coli* ER2537 cells (New England Biolabs, USA), amplified, and then obtained to be ready for use in the next screening step. The procedure was repeated three times by applying the Ang2 polypeptide to a Maxisorp immunotube in amounts of about 10 ug/ml, 1 ug/ml and 0.1 ug/ml, respectively and then, about 600 specific Ang2 bound scFv clones recognizing human Ang2 (Accession #O15123) or mouse Ang2 (Accession #NP_031452) were identified when measured using ELISA (Enzyme-Linked ImmunoSorbent Assay) affinity assay (see Example 2) as described below.

Example 2: Anti-Ang2 Antibody Producing Clone Selection and Antibody Purification Based on binding potential with Ang2 using an ELISA format, 70 clones which produce anti-Ang2 antibodies were selected from the about 600 Ang2 bound scFv clones obtained in Example 1 above. Specifically, clones with high ELISA optical density ("OD") were selected among the clones which can bind to Ang2 and inhibit Tie2 binding. Then, each clone was cultured in SB media to which ampicillin was added up to the level of optical density at 600 nanometers ("OD 600")=1.0, 1 mM IPTG (Isopropyl-β-D-Thiogalactopyranoside) was injected thereto and then, periplasm fractions were collected to partially purify anti-Ang2 monoclonal antibodies using NI-NTA column (QIAGEN).

Example 3: Ang2:Tie2 Neutralization ELISA (Competitive ELISA)

To verify molecular interaction of the bound assemblies, a competitive ELISA was performed. A 96-well MaxiSorp™ flat-bottom plate (Nunc) was coated with 4 ug/ul of hTie2-Fc (R&D Systems), which is a protein with the Fc of human IgG1 bound thereto. After that, the plate was washed five times with 0.05% (v/v) Tween-20-containing PBS (Phosphate Buffer Saline) and then blocked with 1% (v/v) BSA (Bovine serum albumin; Sigma)-containing PBS at a room temperature for 2 hours.

To perform Ang2:Tie2 neutralization ELISA, the anti-Ang2 antibodies in their scfv forms purified in Example 2 (1, 10, 100, and 1000 nM) were added to each well of the plate coated with hTie2-Fc, along with 1% (v/v) BSA and 400 ng/ml of FLAG-Tagged hAng2 and then, the plate was allowed to react at a room temperature for 2 hours. Thereafter, the plate was washed five times with 0.05% Tween-20-containing PBS and then, an HRP-conjugated anti-FLAG antibody (SIGMA) diluted in 1% (v/v) BSA-containing PBS at 1:5,000 ratio (v/v) was added in the amount of 100 ul (microliter) to each well to react at a room temperature for 1 hour, followed by washing five times with 0.1% (v/v) Tween-20-containing PBS. Finally, 100 ul (microliter) of TMB substrate (cell signal) was added to each well of the plate to induce color development at a room temperature for 3 min. Then, the reaction was ceased by the addition of 50 ul of 5N H$_2$SO$_4$ solution and OD450 values were measured on a plate reader (Molecular Devices). Through them, 50% inhibition concentrations (IC50) against Ang2:Tie2 binding were obtained and shown in the following Table 3.

TABLE 3

| Antibody | 50% inhibition concentration against Ang2:Tie2 binding (IC$_{50}$, nM) |
|---|---|
| SAIT-ANG2-AB-2-E6 | 18.9 |
| SAIT-ANG2-AB-4-H10 | 24.3 |
| SAIT-ANG2-AB-8-A5 | 36.3 |
| SAIT-ANG2-AB-7-C9 | 39.7 |
| SAIT-ANG2-AB-3-D3 | 9.9 |
| SAIT-ANG2-AB-4-C11 | 6.5 |
| SAIT-ANG2-AB-4-F5 | 10 |
| SAIT-ANG2-AB-4-F11 | 6.6 |

As in Table 3 above, it was confirmed that the anti-Ang2 antibodies can neutralize binding between Ang2 and Tie2 receptors.

Example 4: Binding ELISA of hAng2 and mAng2

To measure binding of the antibodies prepared above with each antigen, ELISA was performed. A 96-well MaxiSorp™ flat-bottom plate (Nunc) was coated with 5~20 ug/ml of human Ang2 and mouse Ang2 (Accession #NP_031452) (both, R&D Systems). After that, the plate was washed five times with 0.05% (v/v) Tween-20-containing PBS and then blocked with 1% (v/v) BSA-containing PBS at a room temperature for 2 hours. The anti-Ang2 antibodies in their scFv forms prepared above were added to each well of the plate which was then allowed to react at a room temperature for 2 hours.

Thereafter, the plate was washed five times with 0.05% Tween-20-containing PBS and then, an HRP-conjugated anti-HA (HA-probe Antibody (F-7) HRP conjugated) antibody (Santacruz) diluted in 1% (v/v) BSA-containing PBS at 1:1,000 ratio (v/v) was added in the amount of 50 ul to each well to react at a room temperature for 1 hour, followed by washing five times with 0.1% (v/v) Tween-20-containing PBS. Finally, 100 ul of TMB substrate (cell signal) was added to each well of the plate to induce color development at a room temperature for 3 min and then, the reaction was ceased by the addition of 50 ul of 5N H$_2$SO$_4$ solution and OD450 values were measured on a plate reader (Molecular Devices). By obtaining 50% binding concentrations (Kd) to human Ang2 and mouse Ang2 proteins through them, the binding degrees of the anti-Ang2 antibodies to each antigen were measured. The obtained results are shown in the following Table 4.

TABLE 4

| Antibody | human Ang2 (Kd, nM) | mouse Ang2 (Kd, nM) |
|---|---|---|
| SAIT-ANG2-AB-2-E6 | 9.3 | 5.1 |
| SAIT-ANG2-AB-4-H10 | 5.3 | 15.8 |
| SAIT-ANG2-AB-8-A5 | 5.3 | 11.7 |
| SAIT-ANG2-AB-7-C9 | 3.8 | 8.7 |
| SAIT-ANG2-AB-3-D3 | 4.3 | 37.8 |
| SAIT-ANG2-AB-4-C11 | 4.9 | 28.6 |
| SAIT-ANG2-AB-4-F5 | 12.1 | 23.8 |
| SAIT-ANG2-AB-4-F11 | 3 | 20.7 |

Example 5: Ang2 Epitope Mapping

To identify each epitope for the anti-Ang2 antibodies obtained above, ELISA was performed using recombinant proteins in which the receptor binding sites of Ang2 protein were artificially mutated.

A 96-well MaxiSorp™ flat-bottom plate (Nunc) was coated with 50 ul of the anti-Ang2 scFv selected above. After that, the plate was washed five times with 0.05% (v/v) Tween-20-containing PBS and then blocked with 1% (v/v) BSA-containing PBS at a room temperature for 2 hours. S417, Q418, P419, N421, I434, D448, A449, P452, Y460, N467, K468, or F469 residue of Ang2 was mutated with alanine and tagged with FLAG (1012 Da) and then 250 ng of them was each added to each well to the plate, which was allowed to react at a room temperature for 2 hours. Thereafter, the plate was washed five times with 0.05% Tween-20-containing PBS and then, an HRP-conjugated anti-FLAG antibody (SIGMA) diluted in 1% (v/v) BSA-containing PBS at 1:5,000 ratio (v/v) was added in the amount of 50 ul to each well to react at a room temperature for 1 hour, followed by washing five times with 0.1% (v/v) Tween-20-containing PBS. The experiment was conducted under about pH 7.4.

Finally, 100 μl of TMB substrate (cell signal) was added to each well of the plate to induce color development and then, the reaction was ceased by the addition of 50 μl of 5N $H_2SO_4$ solution and OD450 values were measured on a plate reader (Molecular Devices). By comparing binding with mutated Ang2 to binding with unmutated Ang2, each epitope for the Ang2 antibodies was identified. The obtained results are shown in the following Tables 5 and 6.

TABLE 5

|  | Relative binding (%) with Mutant Ang2 compared to the binding with native Ang2 | | | | | |
|---|---|---|---|---|---|---|
|  | I434 | A449 | P452 | Y460 | N467 | K468 | F469 |
| AB-2-E6 | 5.3 | 3.3 | 24.0 | 40.0 | 72.1 | 94.0 | 112.3 |
| AB-4-H10 | 32.9 | 71.0 | 269.8 | 245.8 | 29.8 | 214.5 | 276.7 |
| AB-8-A5 | 4.0 | 30.5 | 86.5 | 91.6 | 90.7 | 101.0 | 101.5 |
| AB-7-C9 | 8.7 | 14.5 | 85.0 | 78.1 | 86.6 | 97.3 | 89.4 |
| AB-3-D3 | 93.4 | 100.6 | 97.3 | 95.1 | 90.9 | 95.9 | 96.4 |
| AB-4-C11 | 7.2 | 4.8 | 70.0 | 74.3 | 81.7 | 94.8 | 102.3 |
| AB-4-F5 | 68.6 | 14.0 | 15.0 | 21.8 | 11.3 | 87.4 | 259.0 |
| AB-4-F11 | 69.0 | 16.7 | 91.6 | 96.1 | 92.0 | 101.5 | 104.9 |
| Control Antibody 1 | 93.3 | 95.8 | 95.4 | 86.7 | 94.4 | 86.9 | 3.2 |

(Of the above table, control antibody 1 is Regeneron Ang2 antibody)

TABLE 6

| Clone # |  | Epitope (binding region) |
|---|---|---|
| 1 | AB-2-E6, AB-7-C9, AB-4-C11 | I434, A449 |
| 2 | AB-8-A5 | I434 |
| 3 | AB-4-F11 | A449 |
| 4 | AB-4-F5 | A449, P452, N467 |

Example 6: Anti-Ang2 Human Antibody Gene Cloning

The gene sequences of heavy chain and light chain variable regions of monoclonal antibodies to be produced from each clone were amplified using a thermocycler (GeneAmp PCR System 9700, Applied Biosystem) from each antibody producing *E. coli* glycerol stock obtained from the above antibody selection results.

PCR Conditions 5 min. at 94° C.;

[1 min. at 94° C., 1 min. at 55° C., and 2 min. at 72° C.]×30 cycles;

6 min. at 72° C.;

Cooling to 4° C.

Primers:

```
pC3X-f: 3'-GCACGACAGGTTTCCCGAC-5',
pC3X-b: 3'-AACCATCGATAGCAGCACCG-5'.
```

The PCR products obtained from each reaction were washed with QIAquick Multiwell PCR Purification kit (Qiagen) according to the Manufacturer's protocol.

The PCR results obtained above were cloned and subjected to DNA sequencing by a well-known method. As a result, CDR sequences shown in the following Table 7 and Table 8 were able to be obtained.

TABLE 7

|  | Amino acid sequence of heavy chain CDR | | |
|---|---|---|---|
| Antibody Name | CDRH1-KABAT | CDRH2-KABAT | CDRH3-KABAT |
| SAIT-ANG2-AB-2-E6 | DYAMS (SEQ ID NO: 1) | AIYPDSGNKYYADSVKG (SEQ ID NO: 9) | ARHSSDPKVKSGYYDDGMDV (SEQ ID NO: 17) |
| SAIT-ANG2-AB-8-A5 | DYYMS (SEQ ID NO: 2) | GIYPSGGSTYYADSVKG (SEQ ID NO: 10) | ARDPSTLTYAGFDY (SEQ ID NO: 18) |
| SAIT-ANG2-AB-7-C9 | NYAMS (SEQ ID NO: 3) | AISSGGGNIYYADSVKG (SEQ ID NO: 11) | AKSGIQPSPPSMSSAYAMDV (SEQ ID NO: 19) |
| SAIT-ANG2-AB-4-C11 | DYAMS (SEQ ID NO: 4) | SIYPDDGNTYYADSVKG (SEQ ID NO: 12) | ARHTSHHTSIDGYYYYGMDG (SEQ ID NO: 20) |

TABLE 7-continued

Amino acid sequence of heavy chain CDR

| Antibody Name | CDRH1-KABAT | CDRH2-KABAT | CDRH3-KABAT |
|---|---|---|---|
| SAIT-ANG2-AB-4-F5 | DYDMS (SEQ ID NO: 5) | SISHGDSNKYYADSVKG (SEQ ID NO: 13) | AKSSGIQESPPTYYYYGMDV (SEQ ID NO: 21) |
| SAIT-ANG2-AB-4-F11 | DYAMS (SEQ ID NO: 6) | SIYPDDGNTYYADSVKG (SEQ ID NO: 14) | AKHPVRLNLHPMYYYYGMDV (SEQ ID NO: 22) |
| SAIT-ANG2-AB-4-H10 | SYDMS (SEQ ID NO: 7) | LISPDSSSIYYADSVKG (SEQ ID NO: 15) | AKDLISFWRGGFDY (SEQ ID NO: 23) |
| SAIT-ANG2-AB-3-D3 | DYDMS (SEQ ID NO: 8) | GISSDDGNTYYADSVKG (SEQ ID NO: 16) | ARPTIDKYTLRGYYSYGMDV (SEQ ID NO: 24) |

TABLE 8

Amino acid sequence of light chain CDR

| Antibody Name | CDRL1-KABAT | CDRL2-KABAT | CDRL3-KABAT |
|---|---|---|---|
| SAIT-ANG2-AB-2-E6 | SGSSSNIGNNAVN (SEQ ID NO: 25) | ADSNRPS (SEQ ID NO: 33) | GSWDYSLSG (SEQ ID NO: 41) |
| SAIT-ANG2-AB-8-A5 | SGSSSNIGNNYVT (SEQ ID NO: 26) | ADSHRPS (SEQ ID NO: 34) | ATWDYSLSG (SEQ ID NO: 42) |
| SAIT-ANG2-AB-7-C9 | SGSSSNIGNNDVY (SEQ ID NO: 27) | ANSHRPS (SEQ ID NO: 35) | GTWDYSLSG (SEQ ID NO: 43) |
| SAIT-ANG2-AB-4-C11 | TGSSSNIGNNDVS (SEQ ID NO: 28) | SDSKRPS (SEQ ID NO: 36) | GSWDYSLSG (SEQ ID NO: 44) |
| SAIT-ANG2-AB-4-F5 | SGSSSNIGSNAVN (SEQ ID NO: 29) | ADSNRPS (SEQ ID NO: 37) | GSWDYSLSG (SEQ ID NO: 45) |
| SAIT-ANG2-AB-4-F11 | TGSSSNIGNNAVS (SEQ ID NO: 30) | SDSQRPS (SEQ ID NO: 38) | ATWDYSLSA (SEQ ID NO: 46) |
| SAIT-ANG2-AB-4-H10 | SGSSSNIGSNYVN (SEQ ID NO: 31) | SDSHRPS (SEQ ID NO: 39) | GAWDDSLSG (SEQ ID NO: 47) |
| SAIT-ANG2-AB-3-D3 | TGSSSNIGSNYVS (SEQ ID NO: 32) | SDNKRPS (SEQ ID NO: 40) | GTWDDSLNG (SEQ ID NO: 48) |

Example 7: Expression and Purification of Intact Antibody

The heavy chain and light chain variable regions obtained in Example 6 above (see Table 9 below) were each cloned into different vectors. The heavy chain variable region was cloned into a vector pOPTI-VAC (Invitrogen) having a CMV promoter (cytomegalovirus promoter) and including the constant region and Fc region of human IgG1. The light chain variable region was cloned into a vector pFUSE2-CLIg-hl2 (Invivogen) having a CMV promoter (cytomegalovirus promoter) and including the constant region of human IgG1.

Specifically, the heavy chain and the vector including it were treated with ecorI (neb) and NheI (neb) restriction enzymes and the light chain and the vector including it were treated with ecorI (neb) and avrII (neb) restriction enzymes and then, they were ligated with a T4 DNA Ligase (New England Biolab) to prepare a heavy chain vector and a light chain vector for human antibody expression including the desirable regions.

The thus obtained heavy chain vector and light chain vector were transfected together into 293-F cells (Invitrogen). The cells were cultured in a serum-free 293-f expression medium (Invitrogen) at 37° C. and on 5 days, the culture medium was collected. As a result of SDS-PAGE, the culture medium obtained from the culture included human antibodies consisting of heavy chains and light chains having variable region sequences set forth in the following Table 9. The culture medium containing the expressed chimeric antibodies was centrifuged at the speed of 1000×g for 10 min to remove the remaining cells and impurities, followed by affinity chromatography using Protein A (GE-Healthcare) having a strong affinity to antibody Fc regions to purify antibodies through a low PH elution.

The amino acid sequences and the nucleotide sequences of the heavy chain variable regions and the light chain variable regions of the antibodies purified above were analyzed and shown in the following Table 9 and Table 10.

TABLE 9

| Antibody | Amino acid sequence of heavy chain variable region | Amino acid sequence of light chain variable region |
|---|---|---|
| SAIT-ANG2-AB-2-E6 | EVQLLESGGGLVQTGGSLRLSCAASGFTFSDYAMSWVRQAPGKGLEWVSAIYPDSGNKYYADSVKGRFTISRDNSKNTLYLQMNSLRAEDTAVYYCARHSSDPKVKSGYYDDGMDVWGQGTLVAVSS (SEQ ID NO: 54) | QSVLTQPPSASGTPGQRVTISCSGSSSNIGNNAVNWYQQLPGTAPKLLIYADSNRPSGVPDRFSGSKSGTSASLAISGLRSEDEADYYCGSWDYSLSGYVFGGGTKLTVLG (SEQ ID NO: 62) |
| SAIT-ANG2-AB-8-A5 | EVQLLESGGGLVQPGGSLRLSCAASGFTFSDYYMSWVRQAPGKGLEWVSGIYPSGGSTYYADSVKGRFTISRDNSKNTLYLQMNSLRAEDTAVYYCARDPSTLTYAGFDYWGQGTLVTVSS (SEQ ID NO: 55) | QSVLTQPPSASGTPGQRVTISCSGSSSNIGNNYVTWYQQLPGTAPKLLIYADSHRPSGVPDRFSGSKSGTSASLAISGLRSEDEADYYCATWDYSLSGYVFGGGTKLTVLG (SEQ ID NO: 63) |
| SAIT-ANG2-AB-7-C9 | EVQLLESGGGLVQPGGSLRLSCAASGFTFSNYAMSWVRQAPGKGLEWVSAISSGGGNIYYADSVKGRFTISRDNSKNTLYLQMNSLRAEDTAVYYCAKSGIQPSPPSMSSAYAMDVWGQGTLVTVSS (SEQ ID NO: 56) | QSVLTQPPSASGTPGQRVTISCSGSSSNIGNNDVYWYQQLPGTAPKLLIYANSHRPSGVPDRFSGSKSGTSASLAISGLRSEDEADYYCGTWDYSLSGYVFGGGTKLTVLG (SEQ ID NO: 64) |
| SAIT-ANG2-AB-4-C11 | EVQLLESGGGLVQPGGSLRLSCAASGFTFSDYAMSWVRQAPGKGLEWVSSIYPDDGNTYYADSVKGRFTISRDNSKNTLYLQMNSLRAEDTAVYYCARHTSHHTSIDGYYYYGMDGWGQGTLVTVSS (SEQ ID NO: 57) | QSVLTQPPSASGTPGQRVTISCTGSSSNIGNNDVSWYQQLPGTAPKLLIYSDSKRPSGVPDRFSGSKSGTSASLAISGLRSEDEADYYCGSWDYSLSGYVFGGGTKLTVLG (SEQ ID NO: 65) |
| SAIT-ANG2-AB-4-F5 | EVQLLESGGGLVQPGGSLRLSCAASGFTFSDYDMSWVRQAPGKGLEWVSSISHGDSNKYYADSVKGRFTISRDNSKNTLYLQMNSLRAEDTAVYYCAKSSGIQESPPTYYYYGMDVWGQGTLVTVSS (SEQ ID NO: 58) | QSVLTQPPSASGTPGQRVTISCSGSSSNIGSNAVNWYQQLPGTAPKLLIYADSNRPSGVPDRFSGSKSGTSASLAISGLRSEDEADYYCGSWDYSLSGYVFGGGTKLTVLG (SEQ ID NO: 66) |
| SAIT-ANG2-AB-4-F11 | EVQLLESGGGLVQTGGSLRLSCAASGFTFSDYAMSWVRQAPGKGLEWVSSIYPDDGNTYYADSVKGRFTISRDNSKNTLYLQMNSLRAEDTAVYYCAKHPVRLNLHPMYYYYGMDVWGQGTLVTVSS (SEQ ID NO: 59) | QSVLTQPPSASGTPGQRVTISCTGSSSNIGNNAVSWYQQLPGTAPKLLIYSDSQRPSGVPDRFSGSKSGTSASLAISGLRSEDEADYYCATWDYSLSAYVFGGGTKLTVLG (SEQ ID NO: 67) |
| SAIT-ANG2-AB-4-H10 | EVQLLESGGGLVQPGGSLRLSCAASGFTFSSYDMSWVRQAPGKGLEWVSLISPDSSSIYYADSVKGRFTISRDNSKNTLYLQMNSLRAEDTAVYYCAKDLISFWRGGFDYWGQGTLVTVSS (SEQ ID NO: 60) | QSVLTQPPSASGTPGQRVTISCSGSSSNIGSNYVNWYQQLPGTAPKLLIYADSNRPSGVPDRFSGSKSGTSASLAISGLRSEDEADYYCGSWDYSLSGYVFGGGTKLTVLG (SEQ ID NO: 68) |
| SAIT-ANG2-AB-3-D3 | EVQLLESGGGLVQPGGSLRLSCAASGFTFSDYDMSWVRQAPGKGLEWVSGISSDDGNTYYADSVKGRFTISRDNSKNTLYLQMNSLRAEDTAVYYCARPTIDKYTLRGYYSYGMDVWGQGTLVTVSS (SEQ ID NO: 61) | QSVLTQPPSASGTPGQRVTISCTGSSSNIGSNYVSWYQQLPGTAPKLLIYSDNKRPSGVPDRFSGSKSGTSASLAISGLRSEDEADYYCGTWDDSLNGYVFGGGTKLTVLG (SEQ ID NO: 69) |

(Of the above Table, portions marked in bold types are CDR1, CDR2, and CDR3 in order)

TABLE 10

| Antibody | Nucleotide sequence of heavy chain variable region | Nucleotide sequence of light chain variable region |
|---|---|---|
| SAIT-ANG2-AB-2-E6 | GAAGTGCAGCTTCTGGAATCAGGCGGTGGACTGGTGCAGCCAGGAGGCAGCCTCAGGCTGTCTTGCGCAGCCAGCGGATTTACCTTCTCCGATTACGCCATGAGCTGGGTTAGACAGGCCCCTGGCAAGGGGCTGGAGTGGGTCAGTGCCATTTACCCCGACTCCGGGAATAAGTATTACGCTGACTCTGTGAAAGGTAGATTCACTATCTCAAGAGACAACTCCAAAAATACATTGTACTTACAGATGAA | CAGTCAGTCCTGACACAGCCCCCTAGTGCTTCCGGAACCCCTGGGCAGAGGGTGACCATCTCATGCTCAGGTAGCTCCAGCAACATTGGAAACAATGCAGTTAATTGGTATCAGCAACTGCCCGGGACCGCCCCAAAGCTTCTGATCTACGCTGATAGTAATAGACCATCTGGAGTGCCTGACAGATTCAGTGGTTCGAAAAGCGGCACTTCTGCATCCTTGGCCATTTCTGGCTTAAGATCTGAAGATGAGGCCGACTAT |

TABLE 10-continued

| Antibody | Nucleotide sequence of heavy chain variable region | Nucleotide sequence of light chain variable region |
| --- | --- | --- |
| | CTCACTGCGCGCTGAGGATACAGCAGTGTATTATTGTGCGCGGCACTCGAGTGATCCTAAGGTCAAAAGCGGATACTATGACGACGGCATGGATGTTTGGGGCCAAGGGACTCTCGTAACCGTGTCTTCT(SEQ ID NO: 71) | TACTGTGGCTCTTGGGACTACTCCCTGAGCGGATATGTGTTTGGGGGCGGAACTAAGCTCACAGTCCTAGGC (SEQ ID NO: 72) |
| SAIT-ANG2-AB-8-A5 | GAGGTCCAGCTGCTCGAATCAGGCGGTGGGCTGGTGCAGCCAGGCGGCTCCCTGAGGTTAAGTTGCGCCGCTTCTGGCTTTACATTTAGCGATTATTACATGTCCTGGGTCCGCCAGGCCCCCGGGAAAGGTCTGGAGTGGGTGAGCGGAATTTACCCTTCCGGGGGAAGCACCTATTACGCGGATTCTGTAAAGGGTAGATTCACTATCTCAAGAGACAATTCTAAGAATACCCTGTATTTGCAGATGAACAGTCTTAGAGCCGAAGCACAGCAGTTTATTATTGTGCAAGAGACCCCAGTACTCTAACCTACGCTGGCTTCGATTACTGGGGACAAGGAACGCTCGTGACAGTGTCAAGC (SEQ ID NO: 73) | CAAAGTGTTCTCACACAGCCGCCATCCGCTTCCGGGACCCCTGGACAGAGAGTGACCATCAGTTGTAGTGGCTCTTCGAGCAATATTGGCAATAACTATGTGACATGGTATCAGCAGCTTCCTGGAACAGCCCCCAAACTGCTCATCTATGCCGACAGCCACAGACCATCAGGTGTCCCCGATAGATTTTCTGGGTCAAAGTCAGGAACTAGCGCAAGCCTGGCCATTTCTGGATTAAGGTCCGAGGACGAAGCTGATTACTATTGCGCAACTTGGGACTACTCTCTGTCTGGTTACGTGTTCGGCGGCGGAACCAAGTTGACGGTCCTAGGC (SEQ ID NO: 74) |
| SAIT-ANG2-AB-7-C9 | GAGGTGCAACTCCTGGAGTCAGGAGGCGGCCTGGTCCAGCCCGGCGGGAGTCTTAGACTCTCGTGTGCCGCAAGCGGGTTTACATTCAGTAACTACGCCATGTCCTGGGTCAGACAGGCTCCTGGAAAGGGACTGGAATGGGTTTCTGCCATTAGCTCCGGCGGAGGTAATATCTATTACGCTGATTCCGTTAAAGGGAGGTTTACAATCTCTCGGGATAACAGCAAAAATACTTTGTATCTGCAGATGAATAGCTTAAGAGCCGAAGACACTGCAGTGTACTACTGCGCGAAGAGCGGTATTCAACCCTCTCCACCATCCATGTCATCAGCTTATGCAATGGACGTATGGGGGCAGGGCACCCTGGTGACCGTGAGTTCT (SEQ ID NO: 75) | CAGAGCGTCCTGACACAACCTCCATCCGCTTCTGGGACGCCTGGACAGAGAGTGACAATTTCTTGCAGCGGCTCATCTTCAAATATTGGAAACAATGACGTTTATTGGTACCAGCAGCTCCCAGGGACCGCCCCCAAAGCTGCTGATCTATGCAAACTCACACAGACCCAGCGGAGTGCCCGATAGATTCAGTGGATCCAAATCCGGCACTAGTGCCAGCTTGGCAATCTCGGGGCTGAGATCTGAAGACGAGGCTGATTACTATTGTGGTACCTGGGATTACTCCTTAAGTGGTTACGTGTTTGGCGGGGGCACTAAGCTTACCGTCCTAGGC (SEQ ID NO: 76) |
| SAIT-ANG2-AB-4-C11 | GAAGTACAGCTGCTGGAGTCGGGTGGTGGACTGGTTCAGCCAGGAGGCTCATTAAGGCTGAGCTGCGCCGCAAGCGGTTTCACTTTTTCTGATTATGCTATGTCCTGGGTCAGACAGGCCCCTGGGAAGGGACTCGAGTGGGTCTCAAGTATTTACCCCGACGATGGAAATACCTACTATGCCGATAGCGTGAAGGGGCGCTTTACAATCTCTAGAGATAATTCTAAAAACACCCTGTACCTTCAAATGAACTCATTGCGGGCAGAAGACACAGCGGTGTACTATTGTGCTAGACACACGTCCCACCATACCAGCATCGACGGCTACTATTATTACGGGATGGACGGCTGGGGCCAGGGCACTCTCGTGACAGTGTCCAGT(SEQ ID NO: 77) | CAGTCAGTCCTGACTCAGCCACCCTCCGCAAGCGGGACACCTGGACAAAGAGTTACTATCTCTTGCACCGGGTCAAGCTCCAATATCGGTAACAATGATGTGAGTTGGTACCAGCAGTTACCAGGCACCGCCCCGAAACTGCTTATTTACTCAGACAGCAAAAGACCCCTCTGGCGTGCCTGACAGATTCTCAGGAAGCAAGAGTGGCACGTCTGCTTCCTTGGCCATTTCGGGTCTGAGATCCGAGGACGAAGCTGATTATTATTGTGAAGCTGGGATTATAGTCTGTCTGGCTACGTGTTTGGGGGCGGAACCAAGCTCACAGTCCTAGGC (SEQ ID NO: 78) |
| IT-ANG2-AB-4-F5 | GAGGTGCAGTTGCTCGAGTCCGGGGGTGGCCTGGTGCAGCCAGGAGGAAGCCTGAGACTGAGCTGCGCAGCCTCAGGTTTCACATTCTCCGATTACGACATGTCCTGGGTTAGGCAAGCCCCCGGCAAGGGGCTGGAATGGGTAAGCTCTATCAGCCACGGCGACAGTAACAAATATTATGCAGACTCTGTTAAGGGACGGTTTACCATTTCACGCGATAACTCAAAGAATACACTGTACCTTCAAATGAATAGTCTCAGAGCTGAAGATACCGCCGTGTATTACTGTGCTAAATCGTCCGAATCCAGGAGAGTCCCCCTACTTATTACTACTATGGGATGGATGTGTGGGGCCAGGGCACCCTGGTCACTGTCTCTTCTGCTAGC (SEQ ID NO: 79) | CAGTCTGTGTTGACCCAGCCCCCTTCTGCATCTGGCACCCCCGGACAGAGAGTCACTATAAGTTGTTCTGGTAGCTCCTCAAATATCGGCTCAAACGCCGTGAATTGGTACCAGCAATTACCAGGAACAGCTCCTAAGCTGCTTATCTATGCAGACAGTAACAGACCAAGCGGCGTTCCTGATAGATTCTCAGGCTCCAAGTCCGGGACTAGTGCCTCGCTGGCTATTAGCGGTCTCAGAAGTGAAGATGAGGCCGATTACTATTGCGGAAGCTGGGACTACTCCCTGAGCGGTATGTGTTTGGAGGAGGGACAAAACTCACCGTCCTAGGC (SEQ ID NO: 80) |

TABLE 10-continued

| Antibody | Nucleotide sequence of heavy chain variable region | Nucleotide sequence of light chain variable region |
|---|---|---|
| SAIT-ANG2-AB-4-F11 | GAGGTGCAACTGCTGGAGAGTGGTG GGGGCCTTGTTCAGCCCGGCGGATC CTTGAGGCTGTCATGCGCTGCGTCTG GCTTTACTTTCAGCGATTACGCAATG AGTTGGGTGAGACAGGCTCCAGGAA AAGGCCTGGAATGGGTCAGCTCCAT TTATCCTGACGATGGTAACACATATT ACGCCGACAGCGTAAAAGGACGGTT CACCATCTCTCGCGATAATTCTAAG AACACCCTGTATCTCCAGATGAATA GCCTGAGAGCAGAAGACACCGCCGT GTACTACTGTGCCAAGCATCCTGTG AGATTAAACCTGCACCCAATGTACT ATTATTACGGCATGGACGTTTGGGG GCAGGGGACACTCGTGACTGTCTCC TCA (SEQ ID NO: 81) | CAGTCTGTGTTAACACAACCTCCAAG TGCATCCGGAACGCCGGGCCAGAGAG TGACTATCAGCTGCACCGGCAGCTCG TCCAATATCGGTAACAACGCAGTTAG TTGGTACCAGCAGCTTCCCGGCACAG CTCCAAAGCTCTTGATTTACAGCGATT CACAAAGACCTAGTGGTGTCCCCGAT AGATTTTCTGGGAGTAAGAGCGGGAC CAGTGCCTCCCTGGCTATATCAGGAC TGAGATCTGAAGATGAGGCTGACTAT TACTGTGCCACTTGGGACTATTCACTC TCTGCCTATGTGTTCGGGGGCGGAAC CAAACTGACAGTCCTAGGC (SEQ ID NO: 82) |
| SAIT-ANG2-AB-4-H10 | GAGGTTCAGTTGCTGGAGAGTGGCG GCGGCTTAGTGCAGCCAGGTGGCAG CCTGCGCCTTTCTTGTGCCGCCAGTG GGTTTACCTTCTCCTCCTACGACATG AGCTGGGTGCGGCAGGCTCCCGGCA AAGGTCTTGAATGGGTGTCACTGAT CAGCCCTGACAGTTCCTCAATCTATT ATGCAGATTCAGTCAAGGGAAGATT TACCATAAGCAGAGATAATTCCAAG AATACTCTGTACCTACAGATGAACT CGCTCAGAGCCGAAGATACCGCAGT CTACTACTGCGCTAAAGACCTGATTT CTTTCTGGAGGGGGGATTCGACTA TTGGGGGCAAGGAACACTCGTAACA GTGTCTAGC (SEQ ID NO: 83) | CAGAGCGTGCTCACCCAACCTCCCAG TGCATCCGGAACGCCTGGTCAGAGAG TGACAATTAGCTGCTCAGGGTCTTCCT CTAACATCGGGTCCAATTATGTCAATT GGTATCAGCAGTTGCCAGGTACAGCT CCCAAACTGCTGATCTACAGTGATTC CCACAGACCTAGCGGCGTTCCAGACA GATTTAGCGGATCCAAGTCGGGAACT TCTGCAAGCCTCGCTATTTCTGGCCTG AGAAGTGAGGACGAAGCCGATTATTA CTGTGGGGCCTGGGACGATTCATTAT CAGGATACGTGTTCGGAGGCGGCACC AAGCTTACTGTCCTAGGC (SEQ ID NO: 84) |
| SAIT-ANG2-AB-3-D3 | GAGGTACAGCTGCTGGAAAGTGGGG GCGGTCTGGTGCAGCCAGGGGGAAG CCTCCGGCTTTCATGCGCCGCAAGC GGCTTTACATTCAGTGACTATGACAT GAGTTGGGTCCGACAAGCCCCCGGA AAGGGCCTGGAGTGGGTGTCTGAA TCTCCTCCGATGACGGCAATACTTAT TACGCTGACTCCGTTAAAGGTAGGT TCACCATCTCTCGCGATAACTCTAA AAACACCCTCTACCTGCAGATGAAT AGCTTGAGGGCAGAAGATACGGCTG TCTACTATTGTGCCAGACCTACAATT GACAAGTACACATTAAGAGGGTATT ATTCATACGGCATGGATGTTTGGGG ACAGGGAACTCTAGTGACCGTGTCC AGC (SEQ ID NO: 85) | CAGTCAGTGCTGACACAGCCTCCAAG CGCTTCCGGGACACCTGGACAAAGAG TTACCATTTCGTGCACCGGATCCTCCT CAAACATCGGTAGCAATTATGTGTCT TGGTACCAGCAGCTCCCCGGGACTGC CCCCAAACTCTTGATCTACAGCGACA ACAAGAGACCATCTGGTGTGCCTGAT AGATTCAGTGGGAGTAAGTCAGGAAC GAGTGCCTCTCTGGCTATTTCTGGCCT GAGAAGCGAAGATGAGGCAGACTATT ATTGTGGCACCTGGGATGACTCCCTG AATGGCTACGTCTTTGGCGGCGGAAC AAAACTTACTGTCCTAGGC (SEQ ID NO: 86) |

Example 8: Ang2:Tie2 Neutralization ELISA (Competitive ELISA)

To verify molecular interaction of the bound assemblies, a competitive ELISA was performed. A 96-well MaxiSorp™ flat-bottom plate (Nunc) was coated with 4 ug/ul of hTie2-Fc (R&D Systems), which is a protein with the Fc of human IgG1 bound thereto. After that, the plate was washed five times with 0.05% (v/v) Tween-20-containing PBS (Phosphate Buffer Saline) and then blocked with 1% (v/v) BSA (Bovine serum albumin; Sigma)-containing PBS at a room temperature for 2 hours.

To perform Ang2:Tie2 neutralization ELISA, the anti-Ang2 antibodies in their IgG forms purified in Example 2 (0.00, 0.01, 0.1, 1, 10, 100, and 1000 nM) were added to each well of the plate coated with hTie2-Fc, along with 1% (v/v) BSA and 400 ng/ml of FLAG-Tagged hAng2 and then, the plate was allowed to react at a room temperature for 2 hours. Thereafter, the plate was washed five times with 0.05% Tween-20-containing PBS and then, an HRP-conjugated anti-FLAG antibody (SIGMA) diluted in 1% (v/v) BSA-containing PBS at 1:5,000 ratio (v/v) was added in the amount of 100 ul to each well to react at a room temperature for 1 hour, followed by washing five times with 0.1% (v/v) Tween-20-containing PBS. Finally, 100 ul of TMB substrate (cell signal) was added to each well of the plate to induce color development at a room temperature for 3 min. Then, the reaction was ceased by the addition of 50 ul of 5N $H_2SO_4$ solution and OD450 values were measured on a plate reader (Molecular Devices). Through them, 50% inhibition concentrations (IC50) against Ang2:Tie2 binding were obtained and shown in the following Table 11.

TABLE 11

| Antibody | 50% inhibition concentration against Ang2:Tie2 binding ($IC_{50}$, nM) |
|---|---|
| SAIT-ANG2-AB-2-E6 | 0.605 |
| SAIT-ANG2-AB-4-H10 | 0.417 |

TABLE 11-continued

| Antibody | 50% inhibition concentration against Ang2:Tie2 binding ($IC_{50}$, nM) |
|---|---|
| SAIT-ANG2-AB-8-A5 | 0.341 |
| SAIT-ANG2-AB-7-C9 | 0.392 |
| SAIT-ANG2-AB-3-D3 | 0.44 |
| SAIT-ANG2-AB-4-C11 | 0.421 |
| SAIT-ANG2-AB-4-F5 | 1.525 |
| SAIT-ANG2-AB-4-F11 | 0.37 |

As in Table 11 above, it was confirmed that the anti-Ang2 antibodies can neutralize binding between Ang2 and Tie2 receptors.

Example 9: Binding ELISA of mAng2

To measure binding of the antibodies prepared above with each antigen, ELISA was performed. A 96-well MaxiSorp™ flat-bottom plate (Nunc) was coated with 5~20 ug/ml of human Ang2 and mouse Ang2 (Accession #NP_031452) (both, R&D Systems). After that, the plate was washed five times with 0.05% (v/v) Tween-20-containing PBS and then blocked with 1% (v/v) BSA-containing PBS at a room temperature for 2 hours. The anti-Ang2 antibodies in their IgG forms prepared above (0.001, 0.01, 0.1, 1, 10, 100, and 1000 nM) were added to each well of the plate which was then allowed to react at a room temperature for 2 hours.

Thereafter, the plate was washed five times with 0.05% Tween-20-containing PBS and then, an HRP-conjugated anti-human FC (Anti-hFc-HRP conjugated) antibody (SIGMA) diluted in 1% (v/v) BSA-containing PBS at 1:5,000 ratio (v/v) was added in the amount of 50 ul to each well to react at a room temperature for 1 hour, followed by washing five times with 0.1% (v/v) Tween-20-containing PBS. Finally, 100 ul of TMB substrate (cell signal) was added to each well of the plate to induce color development at a room temperature for 3 min and then, the reaction was ceased by the addition of 50 ul of 5N $H_2SO_4$ solution and OD450 values were measured on a plate reader (Molecular Devices). By obtaining 50% binding concentrations (Kd) to human Ang2 and mouse Ang2 proteins through them, the binding degrees of the anti-Ang2 antibodies to each antigen were measured. The obtained results are shown in the following Table 12.

TABLE 12

| Antibody | mouse Ang2 (Kd, nM) |
|---|---|
| SAIT-ANG2-AB-2-E6 | 0.35 |
| SAIT-ANG2-AB-4-H10 | 0.21 |
| SAIT-ANG2-AB-8-A5 | 0.19 |
| SAIT-ANG2-AB-3-D3 | 0.30 |
| SAIT-ANG2-AB-4-C11 | 0.28 |
| SAIT-ANG2-AB-4-F11 | 0.36 |

Example 10: Antigen Affinity (Kd Values) Measurement Using Surface Plasmon Resonance (SPR) Method To measure accurate affinities toward an anti-Ang2 antigen, antigen affinities were measured by a SPR method using a BIAcore T100 (GE Healthcare). The SPR method uses refractive index change of light which passes a sensor chip according to the state of materials coated onto the sensor chip, and if an antigen or an antibody is flowed onto a chip coated with the antigen or antibody, it causes changes in refractive index due to their binding and Kd values are thus calculated from the measured values.

First, anti-His antibody was immobilized on a CM5 sensor chip (GE healthcare) up to 8,000 RU levels using a pH 5.0 acetate solution and an amine coupling kit (GE Healthcare). A recombinant hAng2 (C-His, R&D Systems) protein was flowed onto the chip to be captured at 100 to 200 RU levels. The antibodies obtained in Example 2 above were diluted serially to twice each time starting from 100 nM concentration and each of them was flowed onto the chip to allow them to be bound to (on), dissociated from (off), and regenerated (using 10 mM NaOH solution) from the antigen captured on the sensor chip, thereby to measure antigen-antibody affinities. The results are as shown in the following Table 13.

TABLE 13

| Antibody | On rate (1/Ms) | Off Rate (1/s) | Affinity (Kd, nM) |
|---|---|---|---|
| SAIT-ANG2-AB-2-E6 | $1.220 \times 10^6$ | $7.950 \times 10^{-4}$ | 0.65 |
| SAIT-ANG2-AB-4-H10 | $2.812 \times 10^6$ | $3.328 \times 10^{-4}$ | 0.118 |
| SAIT-ANG2-AB-8-A5 | $4.396 \times 10^6$ | $3.266 \times 10^{-4}$ | 0.074 |
| SAIT-ANG2-AB-7-C9 | $1.785 \times 10^6$ | $3.661 \times 10^{-4}$ | 0.205 |
| SAIT-ANG2-AB-3-D3 | $1.162 \times 10^6$ | $5.461 \times 10^{-4}$ | 0.47 |
| SAIT-ANG2-AB-4-C11 | $8.327 \times 10^5$ | $4.899 \times 10^{-4}$ | 0.588 |
| SAIT-ANG2-AB-4-F5 | $1.895 \times 10^6$ | 0.001117 | 0.589 |
| SAIT-ANG2-AB-4-F11 | $1.765 \times 10^6$ | $7.774 \times 10^{-4}$ | 0.44 |

Example 11: Ang2 Receptor Activity Inhibitory Test of Ang2 Antibodies

As Ang2 induces a change in vascular endothelial cells by binding to a Tie2 receptor expressed in the vascular endothelial cells to induce the phosphorylation of the receptor and activate it, the Ang2 inhibitory activities of the anti-Ang2 antibodies were verified through the functional analysis of the antibodies using a cell-based assay.

For this, $1 \times 10^6$ of HUVEC (ATCC) cells (Kim et al., *Biochim Biophys Acta.*, 2009) were cultured in a 60 mm culture dish using 5% (v/v) FBS (Gibco)-added EGM-2 (Endothelial growth media) media (Lonza) at 37° C. and when they reached 80~90% confluency, the media were replaced with serum-free EGM-2 media and cultured at 37° C. for 16 hours. The dish was washed once with PBS and after the replacement with 0.1 nM sodium orthovanadate-mixed EGM-2 media, they were further cultured for 10 min. After washed once with PBS, the cultured cells were treated with a mixture prepared by mixing the anti-Ang2 antibodies prepared in Example 2 at a 10 ug/ml concentration with 2 ug/ml human Ang2 protein (R&D systems) and letting them stand for 20 min and further cultured for 10 min.

The cells were washed using a cold PBS, treated with 300 ul of lysis buffer (Roche), collected to a tube to allow them to be dissolved at 4° C. for 30 min. and then, centrifuged at 13,000 rpm for 15 min. to measure a supernatant. 2 ug of anti Tie2 antibody (R&D system) was added to 0.5 mg of a cell lysate, which was then overnight reacted at 4° C. and then subjected to immunoprecipitation by the addition of protein A bead (GE Healthcare) thereto.

The reactant obtained above was centrifuged at 13,000 rpm for 15 min. to obtain a pellet, which was washed two to three times with lysis buffer (Roche), added to a sample buffer (Invitrogen) mixed with a reducing agent, and boiled at 95° C. for 5 min., and then, applied to NuPAGE Novex 4-12% Bis-Tris gel (Invitrogen) and transferred onto Nitrocellulose membrane (Invitrogen).

To verify the presence of the phosphorylation of Tie2, the above blots were blocked with PBST mixed with 3% (v/v) skim milk (Sigma) for 30 min. and identified using an HRP-conjugated anti-phospho tyrosine antibody (Millipore). For Tie2 identification, the blots were reacted in a stripping buffer (Thermo) for 15 min and then blocked again and identified using an anti Tie2 antibody (Santa cruz). After band intensities were measured using Image J software (http://rsb.info.nih.gov/ij/index.html), the inhibitory degrees of Tie2 phosphorylation after the treatment of the anti-Ang2 antibodies were calculated in relative % against the Ang2 single treatment group, and the results are shown in the following Table 14.

TABLE 14

| Antibody (treated amount: 50 nM) | Tie2 phosphorylation inhibition (%) |
|---|---|
| SAIT-ANG2-AB-4-H10 | 69% |
| SAIT-ANG2-AB-8-A5 | 60% |
| SAIT-ANG2-AB-2-E6 | 62% |

Example 12: Inhibition Test of Binding Between Ang2 and Integrin

An ELISA plate was coated with a diluting solution of integrin (alpha5beta1 ($\alpha 5\beta 1$ ($\alpha 5$: NCBI Accession No. P08648, $\beta 1$: NCBI Accession No. P05556); R&D systems) protein diluted in PBS at a concentration of 5 ug/ml (18 hours, 4° C.) and then blocked with 1% (v/v) BSA at a room temperature for 2 hours. Thereafter, the plate was treated with Ang2 protein (FLAG-Ang2, 0.05 ml of Ang2 protein solution diluted in PBS at a concentration of 10 ug/ml) tagged with a FLAG sequence (DYKDDDDK, Sigma) at N-terminal and an antibody (0.05 ml of antibody solution diluted in PBS at a concentration of 10 ug/ml) at the same time, incubated at a room temperature for 2 hours, and washed five times with PBS-t (0.1% (v/v) triton X-100 in PBS). After that, an anti-FLAG antibody (Sigma) conjugated with horseradish peroxidase (HRP) was added to react, and the plate was washed again five times with PBS-t. Bindings between Ang2 and the above the integrin were identified indirectly by measuring the amounts of the anti-FLAG antibody remaining in the ELISA plate via color development using TMB (3,3,5,5-tetramethylbenzidine) as a substrate of HRP. As positive controls, control antibody 1 ((Regeneron Ang2 antibody) and control antibody 2 (Astra Zeneca Ang2 antibody) were used. Also, to show the background, a group coated with BSA instead of integrin was used.

Figure 2:
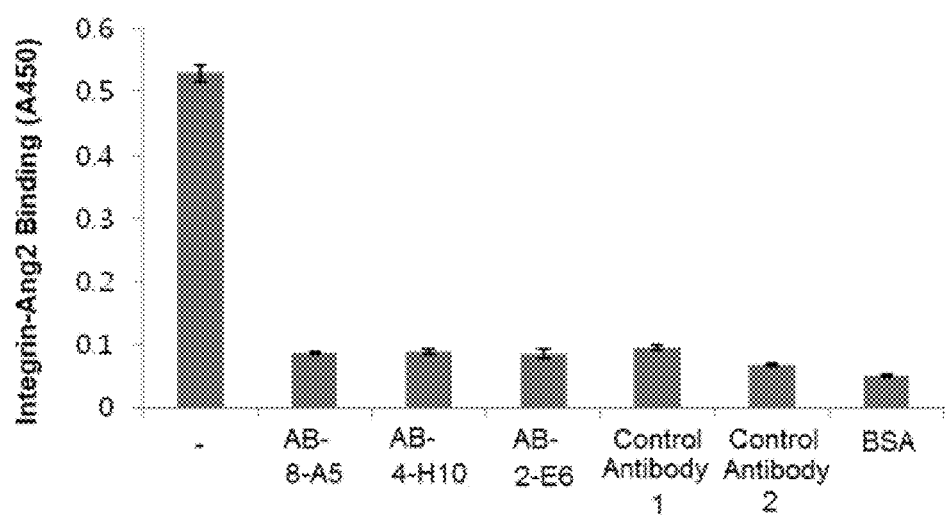
FIG. 2 is a graph showing binding between Ang2 and an integrin according to the treatment of an anti-Ang2 antibody (control antibody 1: Regeneron Ang2 antibody, control antibody 2: Astra Zeneca Ang2 antibody).

The results obtained above were shown in FIG. 2. As seen in FIG. 2, the anti-Ang2 antibodies provided in the invention remarkably suppressed binding between integrin and Ang2.

Example 13: Animal Test of Colorectal Cancer Proliferation Suppression of Anti Ang2 Antibody To see anticancer effects resulting from the cancer cell proliferation suppression of 10 kinds of monoclonal antibodies obtained in Example 7 above, it was tested whether the administration of the monoclonal antibodies causes a decrease in the size of tumor in vivo in a xenograft mouse animal model into which human colorectal cancer cell line was administered.

$5 \times 10^6$ human colorectal cancer cell line Colo205 (ATCC, CCL-222) were suspended in PBS and 50 ul of them were injected into 6-week-old female BALB/c nude mice (Shanghai SLAC Laboratory Animal Co. Ltd.) via a subcutaneous injection and then, 6 mice with cancer size of 50-150 mm$^3$ were selected from each group and used as a mouse animal model for the following experiment. 1-2 weeks later after cancer cells were generated (before/after tumor volume 100 mm$^3$), each antibody was suspended at a 1 mg/ml concentration in PBS and 200 to 250 ul thereof were administered into the mice via an intraperitoneal injection. Upon IV administration 1~2 times weekly, the growth (size and weight) of tumors was measured at a 10 mg/kg concentration and shown in FIG. 3.

The size of tumor (V) was calculated using the following formula:

$$V = (\text{length} \times \text{width}^2)/2$$

Figure 3:
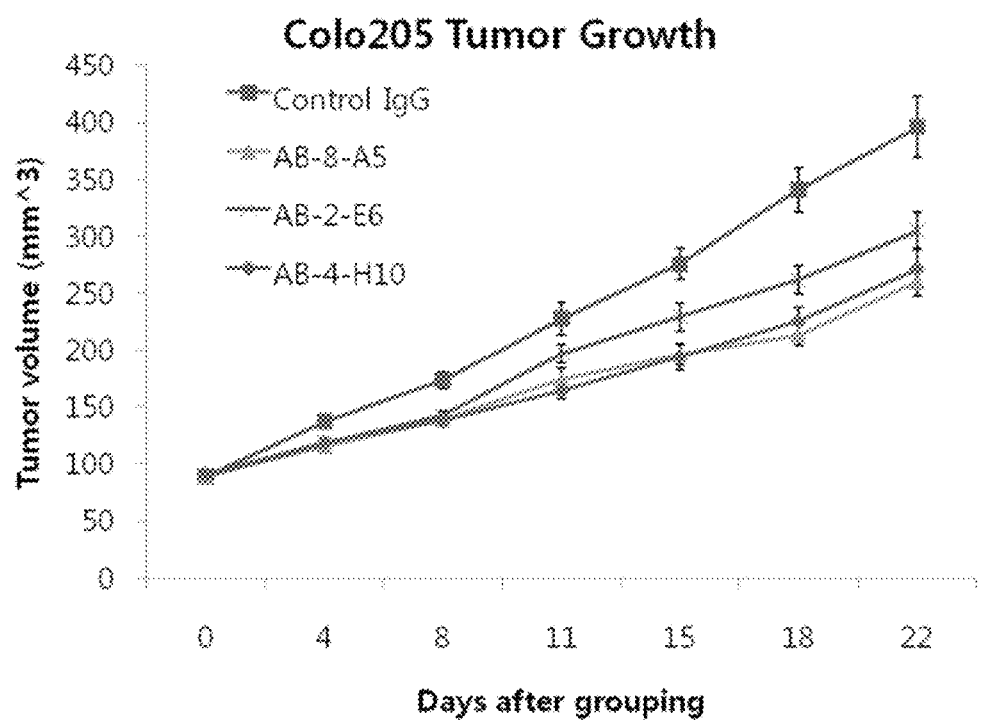
FIG. 3 is a graph showing tumor growth according to treatment with an anti-Ang2 antibody.

As seen in FIG. 3, the growth of tumors in the antibody treatment groups was remarkably reduced in comparison with the control group.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-Ang2 antibody or an antigen-binding fragment thereof comprising
 i) a CDR-H1 comprising SEQ ID NO: 1,
  a CDR-H2 comprising SEQ ID NO: 9,
  a CDR-H3 comprising SEQ ID NO: 17,
  a CDR-L1 comprising SEQ ID NO: 25,
  a CDR-L2 comprising SEQ ID NO: 33, and
  a CDR-L3 comprising SEQ ID NO: 41;
 ii) a CDR-H1 comprising SEQ ID NO: 2,
  a CDR-H2 comprising SEQ ID NO: 10,
  a CDR-H3 comprising SEQ ID NO: 18,
  a CDR-L1 comprising SEQ ID NO: 26,
  a CDR-L2 comprising SEQ ID NO: 34, and
  a CDR-L3 comprising SEQ ID NO: 42;
 iii) a CDR-H1 comprising SEQ ID NO: 3,
  a CDR-H2 comprising SEQ ID NO: 11,
  a CDR-H3 comprising SEQ ID NO: 19,
  a CDR-L1 comprising SEQ ID NO: 27,
  a CDR-L2 comprising SEQ ID NO: 35, and
  a CDR-L3 comprising SEQ ID NO: 43;
 iv) a CDR-H1 comprising SEQ ID NO: 4,
  a CDR-H2 comprising SEQ ID NO: 12,
  a CDR-H3 comprising SEQ ID NO: 20,
  a CDR-L1 comprising SEQ ID NO: 28,
  a CDR-L2 comprising SEQ ID NO: 36, and
  a CDR-L3 comprising SEQ ID NO: 44;

v) a CDR-H1 comprising SEQ ID NO: 5,
   a CDR-H2 comprising SEQ ID NO: 13,
   a CDR-H3 comprising SEQ ID NO: 21,
   a CDR-L1 comprising SEQ ID NO: 29,
   a CDR-L2 comprising SEQ ID NO: 37, and
   a CDR-L3 comprising SEQ ID NO: 45;

vi) a CDR-H1 comprising SEQ ID NO: 6,
   a CDR-H2 comprising SEQ ID NO: 14,
   a CDR-H3 comprising SEQ ID NO: 22,
   a CDR-L1 comprising SEQ ID NO: 30,
   a CDR-L2 comprising SEQ ID NO: 38, and
   a CDR-L3 comprising SEQ ID NO: 46;

vii) a CDR-H1 comprising SEQ ID NO: 7,
   a CDR-H2 comprising SEQ ID NO: 15,
   a CDR-H3 comprising SEQ ID NO: 23,
   a CDR-L1 comprising SEQ ID NO: 31,
   a CDR-L2 comprising SEQ ID NO: 39, and
   a CDR-L3 comprising SEQ ID NO: 47;
or
viii) a CDR-H1 comprising SEQ ID NO: 8,
   a CDR-H2 comprising SEQ ID NO: 16,
   a CDR-H3 comprising SEQ ID NO: 24,
   a CDR-L1 comprising SEQ ID NO: 32,
   a CDR-L2 comprising SEQ ID NO: 40, and
   a CDR-L3 comprising SEQ ID NO: 48.

2. The anti-Ang2 antibody or an antigen-binding fragment thereof as claimed in claim 1, wherein the antibody or antigen-binding fragment thereof comprises:
   a heavy chain variable region comprising SEQ ID NO: 54 and a light chain variable region comprising SEQ ID NO: 62;
   a heavy chain variable region comprising SEQ ID NO: 55 and a light chain variable region comprising SEQ ID NO: 63;
   a heavy chain variable region comprising SEQ ID NO: 56 and a light chain variable region comprising SEQ ID NO: 64;
   a heavy chain variable region comprising SEQ ID NO: 57 and a light chain variable region comprising SEQ ID NO: 65;
   a heavy chain variable region comprising SEQ ID NO: 58 and a light chain variable region comprising SEQ ID NO: 66;
   a heavy chain variable region comprising SEQ ID NO: 59 and a light chain variable region comprising SEQ ID NO: 67;
   a heavy chain variable region comprising SEQ ID NO: 60 and a light chain variable region comprising SEQ ID NO: 68;
   or
   a heavy chain variable region comprising SEQ ID NO: 61 and a light chain variable region comprising SEQ ID NO: 69.

3. A pharmaceutical composition comprising the anti-Ang2 antibody or an antigen-binding fragment thereof as claimed in claim 1.

4. A method of treating a colorectal cancer, the method comprising administering to a subject in need thereof the anti-Ang2 antibody or an antigen-binding fragment thereof as claimed in claim 1.

5. The method as claimed in claim 4, wherein the colorectal cancer comprises colorectal metastasis or colorectal invasion.

6. A method for detecting Ang2 comprising:
   treating a biological sample with the anti-Ang2 antibody or the antigen-binding fragment thereof as claimed in claim 1; and
   identifying the presence of an antigen-antibody reaction.

* * * * *

SEQUENCE LISTING

<160> NUMBER OF SEQ ID NOS: 88

<210> SEQ ID NO 1
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 1

Asp Tyr Ala Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 2

Asp Tyr Tyr Met Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 3

Asn Tyr Ala Met Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 4

Asp Tyr Ala Met Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 5

Asp Tyr Asp Met Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 6

Asp Tyr Ala Met Ser
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 7

Ser Tyr Asp Met Ser
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 8

Asp Tyr Asp Met Ser
1               5

<210> SEQ ID NO 9
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 9

Ala Ile Tyr Pro Asp Ser Gly Asn Lys Tyr Tyr Ala Asp Ser Val Lys
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 10

Gly Ile Tyr Pro Ser Gly Gly Ser Thr Tyr Tyr Ala Asp Ser Val Lys
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 11

Ala Ile Ser Ser Gly Gly Gly Asn Ile Tyr Tyr Ala Asp Ser Val Lys
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)

```
<400> SEQUENCE: 12

Ser Ile Tyr Pro Asp Asp Gly Asn Thr Tyr Tyr Ala Asp Ser Val Lys
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 13

Ser Ile Ser His Gly Asp Ser Asn Lys Tyr Tyr Ala Asp Ser Val Lys
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 14

Ser Ile Tyr Pro Asp Asp Gly Asn Thr Tyr Tyr Ala Asp Ser Val Lys
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 15

Leu Ile Ser Pro Asp Ser Ser Ser Ile Tyr Tyr Ala Asp Ser Val Lys
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 16

Gly Ile Ser Ser Asp Asp Gly Asn Thr Tyr Tyr Ala Asp Ser Val Lys
1               5                   10                  15

Gly

<210> SEQ ID NO 17
<211> LENGTH: 20
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 17

Ala Arg His Ser Ser Asp Pro Lys Val Lys Ser Gly Tyr Tyr Asp Asp
```

```
1               5                   10                  15

Gly Met Asp Val
            20

<210> SEQ ID NO 18
<211> LENGTH: 14
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 18

Ala Arg Asp Pro Ser Thr Leu Thr Tyr Ala Gly Phe Asp Tyr
1               5                   10

<210> SEQ ID NO 19
<211> LENGTH: 20
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 19

Ala Lys Ser Gly Ile Gln Pro Ser Pro Ser Met Ser Ser Ala Tyr
1               5                   10                  15

Ala Met Asp Val
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 20

Ala Arg His Thr Ser His His Thr Ser Ile Asp Gly Tyr Tyr Tyr Tyr
1               5                   10                  15

Gly Met Asp Gly
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 21

Ala Lys Ser Ser Gly Ile Gln Glu Ser Pro Pro Thr Tyr Tyr Tyr Tyr
1               5                   10                  15

Gly Met Asp Val
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 22

Ala Lys His Pro Val Arg Leu Asn Leu His Pro Met Tyr Tyr Tyr Tyr
1               5                   10                  15
```

Gly Met Asp Val
        20

<210> SEQ ID NO 23
<211> LENGTH: 14
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 23

Ala Lys Asp Leu Ile Ser Phe Trp Arg Gly Gly Phe Asp Tyr
1               5                   10

<210> SEQ ID NO 24
<211> LENGTH: 20
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 24

Ala Arg Pro Thr Ile Asp Lys Tyr Thr Leu Arg Gly Tyr Tyr Ser Tyr
1               5                   10                  15

Gly Met Asp Val
        20

<210> SEQ ID NO 25
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 25

Ser Gly Ser Ser Ser Asn Ile Gly Asn Asn Ala Val Asn
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 26

Ser Gly Ser Ser Ser Asn Ile Gly Asn Asn Tyr Val Thr
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 27

Ser Gly Ser Ser Ser Asn Ile Gly Asn Asn Asp Val Tyr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 28

Thr Gly Ser Ser Ser Asn Ile Gly Asn Asn Asp Val Ser
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 29

Ser Gly Ser Ser Ser Asn Ile Gly Ser Asn Ala Val Asn
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 30

Thr Gly Ser Ser Ser Asn Ile Gly Asn Asn Ala Val Ser
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 31

Ser Gly Ser Ser Ser Asn Ile Gly Ser Asn Tyr Val Asn
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 32

Thr Gly Ser Ser Ser Asn Ile Gly Ser Asn Tyr Val Ser
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 33

Ala Asp Ser Asn Arg Pro Ser
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 34

```
Ala Asp Ser His Arg Pro Ser
1               5
```

<210> SEQ ID NO 35
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 35

```
Ala Asn Ser His Arg Pro Ser
1               5
```

<210> SEQ ID NO 36
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 36

```
Ser Asp Ser Lys Arg Pro Ser
1               5
```

<210> SEQ ID NO 37
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 37

```
Ala Asp Ser Asn Arg Pro Ser
1               5
```

<210> SEQ ID NO 38
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 38

```
Ser Asp Ser Gln Arg Pro Ser
1               5
```

<210> SEQ ID NO 39
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 39

```
Ser Asp Ser His Arg Pro Ser
1               5
```

<210> SEQ ID NO 40
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 40

```
Ser Asp Asn Lys Arg Pro Ser
1               5
```

<210> SEQ ID NO 41
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 41

```
Gly Ser Trp Asp Tyr Ser Leu Ser Gly
1               5
```

<210> SEQ ID NO 42
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 42

```
Ala Thr Trp Asp Tyr Ser Leu Ser Gly
1               5
```

<210> SEQ ID NO 43
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 43

```
Gly Thr Trp Asp Tyr Ser Leu Ser Gly
1               5
```

<210> SEQ ID NO 44
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 44

```
Gly Ser Trp Asp Tyr Ser Leu Ser Gly
1               5
```

<210> SEQ ID NO 45
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 45

```
Gly Ser Trp Asp Tyr Ser Leu Ser Gly
1               5
```

<210> SEQ ID NO 46
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 46

```
Ala Thr Trp Asp Tyr Ser Leu Ser Ala
```

<210> SEQ ID NO 47
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 47

Gly Ala Trp Asp Asp Ser Leu Ser Gly
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 48

Gly Thr Trp Asp Asp Ser Leu Asn Gly
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)
<220> FEATURE:
<221> NAME/KEY: MOD_RES
<222> LOCATION: (1)..(1)
<223> OTHER INFORMATION: Xaa is Asp (D), Ser(S), or Asn(N)
<220> FEATURE:
<221> NAME/KEY: MOD_RES
<222> LOCATION: (3)..(3)
<223> OTHER INFORMATION: Xaa is Ala(A), Asp(D), or Tyr(Y)

<400> SEQUENCE: 49

Xaa Tyr Xaa Met Ser
1               5

<210> SEQ ID NO 50
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)
<220> FEATURE:
<221> NAME/KEY: MOD_RES
<222> LOCATION: (1)..(1)
<223> OTHER INFORMATION: Xaa is Ala(A), Gly(G), Leu(L), or Ser(S)
<220> FEATURE:
<221> NAME/KEY: MOD_RES
<222> LOCATION: (3)..(3)
<223> OTHER INFORMATION: Xaa is Tyr(Y) or Ser(S)
<220> FEATURE:
<221> NAME/KEY: MOD_RES
<222> LOCATION: (4)..(4)
<223> OTHER INFORMATION: Xaa is Pro(P), His(H), or Ser(S)
<220> FEATURE:
<221> NAME/KEY: MOD_RES
<222> LOCATION: (5)..(5)
<223> OTHER INFORMATION: Xaa is Asp (D), Gly(G), or Ser(S)
<220> FEATURE:
<221> NAME/KEY: MOD_RES
<222> LOCATION: (6)..(6)
<223> OTHER INFORMATION: Xaa is Ser(S), Gly(G), or Asp(D)
<220> FEATURE:
<221> NAME/KEY: MOD_RES
<222> LOCATION: (7)..(7)

<223> OTHER INFORMATION: Xaa is Gly(G) or Ser(S)
<220> FEATURE:
<221> NAME/KEY: MOD_RES
<222> LOCATION: (8)..(8)
<223> OTHER INFORMATION: Xaa is Asn(N) or Ser(S)
<220> FEATURE:
<221> NAME/KEY: MOD_RES
<222> LOCATION: (9)..(9)
<223> OTHER INFORMATION: Xaa is Lys(K), Ile(I), or Thr(T)

<400> SEQUENCE: 50

Xaa Ile Xaa Xaa Xaa Xaa Xaa Xaa Xaa Tyr Tyr Ala Asp Ser Val Lys
1               5                   10                  15

Gly

<210> SEQ ID NO 51
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)
<220> FEATURE:
<221> NAME/KEY: MOD_RES
<222> LOCATION: (1)..(1)
<223> OTHER INFORMATION: Xaa is Ser(S) or Thr(T)
<220> FEATURE:
<221> NAME/KEY: MOD_RES
<222> LOCATION: (9)..(9)
<223> OTHER INFORMATION: Xaa is Asn(N) or Ser(S)
<220> FEATURE:
<221> NAME/KEY: MOD_RES
<222> LOCATION: (11)..(11)
<223> OTHER INFORMATION: Xaa is Ala(A), Tyr(Y), or Asp(D)
<220> FEATURE:
<221> NAME/KEY: MOD_RES
<222> LOCATION: (13)..(13)
<223> OTHER INFORMATION: Xaa is Asn(N), Ser(S), Thr(T), or Tyr(Y)

<400> SEQUENCE: 51

Xaa Gly Ser Ser Ser Asn Ile Gly Xaa Asn Xaa Val Xaa
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)
<220> FEATURE:
<221> NAME/KEY: MOD_RES
<222> LOCATION: (1)..(1)
<223> OTHER INFORMATION: Xaa is Ala(A) or Ser(S)
<220> FEATURE:
<221> NAME/KEY: MOD_RES
<222> LOCATION: (2)..(2)
<223> OTHER INFORMATION: Xaa is Asp(D) or Asn(N)
<220> FEATURE:
<221> NAME/KEY: MOD_RES
<222> LOCATION: (3)..(3)
<223> OTHER INFORMATION: Xaa is Ser(S) or Asn(N)
<220> FEATURE:
<221> NAME/KEY: MOD_RES
<222> LOCATION: (4)..(4)
<223> OTHER INFORMATION: Xaa is Asn(N), Lys(K), His(H), or Gln(Q)

<400> SEQUENCE: 52

Xaa Xaa Xaa Xaa Arg Pro Ser
1               5

<210> SEQ ID NO 53
<211> LENGTH: 9
<212> TYPE: PRT

```
<213> ORGANISM: Artificial Sequence
<220> FEATURE:
<223> OTHER INFORMATION: Synthetic (CDR-L2 of anti-Ang2 antibody)
<220> FEATURE:
<221> NAME/KEY: MOD_RES
<222> LOCATION: (1)..(1)
<223> OTHER INFORMATION: Xaa is Gly(G) or Ala(A)
<220> FEATURE:
<221> NAME/KEY: MOD_RES
<222> LOCATION: (2)..(2)
<223> OTHER INFORMATION: Xaa is Ser(S), Ala(A), or Thr(T)
<220> FEATURE:
<221> NAME/KEY: MOD_RES
<222> LOCATION: (5)..(5)
<223> OTHER INFORMATION: Xaa is Tyr(Y), or Asp(D)
<220> FEATURE:
<221> NAME/KEY: MOD_RES
<222> LOCATION: (8)..(8)
<223> OTHER INFORMATION: Xaa is Ser(S) or Asn(N)
<220> FEATURE:
<221> NAME/KEY: MOD_RES
<222> LOCATION: (9)..(9)
<223> OTHER INFORMATION: Xaa is Gly(G) or Ala(A)

<400> SEQUENCE: 53

Xaa Xaa Trp Asp Xaa Ser Leu Xaa Xaa
1               5

<210> SEQ ID NO 54
<211> LENGTH: 127
<212> TYPE: PRT
<213> ORGANISM: Artificial Sequence
<220> FEATURE:
<223> OTHER INFORMATION: Synthetic Heavy chain variable region of
      anti-Ang2 antibody 2-E6)

<400> SEQUENCE: 54

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ala Ile Tyr Pro Asp Ser Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ser Ser Asp Pro Lys Val Lys Ser Gly Tyr Tyr Asp Asp
            100                 105                 110

Gly Met Asp Val Trp Gly Gln Gly Thr Leu Val Ala Val Ser Ser
        115                 120                 125

<210> SEQ ID NO 55
<211> LENGTH: 121
<212> TYPE: PRT
<213> ORGANISM: Artificial Sequence
<220> FEATURE:
<223> OTHER INFORMATION: Synthetic (Heavy chain variable region of
      anti-Ang2 antibody 8-A5)

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
```

```
            20                  25                  30
Tyr Met Ser Trp Val Arg Gln Ala Pro Gly Lys Gly Leu Glu Trp Val
        35                  40                  45

Ser Gly Ile Tyr Pro Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ser Thr Leu Thr Tyr Ala Gly Phe Asp Tyr Trp Gly
                100                 105                 110

Gln Gly Thr Leu Val Thr Val Ser Ser
            115                 120

<210> SEQ ID NO 56
<211> LENGTH: 127
<212> TYPE: PRT
<213> ORGANISM: Artificial Sequence
<220> FEATURE:
<223> OTHER INFORMATION: Synthetic (Heavy chain variable region of
      anti-Ang2 antibody 7-C9)

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Ser Gly Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Ile Gln Pro Pro Ser Met Ser Ser Ala Tyr
                100                 105                 110

Ala Met Asp Val Trp Gly Gln Gly Thr Leu Val Thr Val Ser Ser
            115                 120                 125

<210> SEQ ID NO 57
<211> LENGTH: 127
<212> TYPE: PRT
<213> ORGANISM: Artificial Sequence
<220> FEATURE:
<223> OTHER INFORMATION: Synthetic (Heavy chain variable region of
      anti-Ang2 antibody 4-C11)

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ser Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Arg His Thr Ser His His Thr Ser Ile Asp Gly Tyr Tyr Tyr Tyr
            100                 105                 110

Gly Met Asp Gly Trp Gly Gln Gly Thr Leu Val Thr Val Ser Ser
            115                 120                 125

<210> SEQ ID NO 58
<211> LENGTH: 127
<212> TYPE: PRT
<213> ORGANISM: Artificial Sequence
<220> FEATURE:
<223> OTHER INFORMATION: Synthetic (Heavy chain variable region of
      anti-Ang2 antibody 4-F5)

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Asp Met Ser Trp Val Arg Gln Ala Pro Gly Lys Gly Leu Glu Trp Val
            35                  40                  45

Ser Ser Ile Ser His Gly Asp Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Gly Ile Gln Glu Ser Pro Pro Thr Tyr Tyr Tyr Tyr
            100                 105                 110

Gly Met Asp Val Trp Gly Gln Gly Thr Leu Val Thr Val Ser Ser
            115                 120                 125

<210> SEQ ID NO 59
<211> LENGTH: 127
<212> TYPE: PRT
<213> ORGANISM: Artificial Sequence
<220> FEATURE:
<223> OTHER INFORMATION: Synthetic (Heavy chain variable region of
      anti-Ang2 antibody 4-F11)

<400> SEQUENCE: 59

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
                20                  25                  30

Ala Met Ser Trp Val Arg Gln Ala Pro Gly Lys Gly Leu Glu Trp Val
            35                  40                  45

Ser Ser Ile Tyr Pro Asp Asp Gly Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Pro Val Arg Leu Asn Leu His Pro Met Tyr Tyr Tyr Tyr
            100                 105                 110

Gly Met Asp Val Trp Gly Gln Gly Thr Leu Val Thr Val Ser Ser
```

<210> SEQ ID NO 60
<211> LENGTH: 121
<212> TYPE: PRT
<213> ORGANISM: Artificial Sequence
<220> FEATURE:
<223> OTHER INFORMATION: Synthetic (Heavy chain variable region of anti-Ang2 antibody 4-H10)

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Leu Ile Ser Pro Asp Ser Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Ile Ser Phe Trp Arg Gly Phe Asp Tyr Trp Gly
            100                 105                 110

Gln Gly Thr Leu Val Thr Val Ser Ser
        115                 120

<210> SEQ ID NO 61
<211> LENGTH: 127
<212> TYPE: PRT
<213> ORGANISM: Artificial Sequence
<220> FEATURE:
<223> OTHER INFORMATION: Synthetic (Heavy chain variable region of anti-Ang2 antibody 3-D3)

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Gly Ile Ser Ser Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Thr Ile Asp Lys Tyr Thr Leu Arg Gly Tyr Tyr Ser Tyr
            100                 105                 110

Gly Met Asp Val Trp Gly Gln Gly Thr Leu Val Thr Val Ser Ser
        115                 120                 125

<210> SEQ ID NO 62
<211> LENGTH: 111
<212> TYPE: PRT
<213> ORGANISM: Artificial Sequence
<220> FEATURE:
<223> OTHER INFORMATION: Synthetic (Light chain variable region of anti-Ang2 antibody 2-E6)

<400> SEQUENCE: 62

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Ala Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 63
<211> LENGTH: 111
<212> TYPE: PRT
<213> ORGANISM: Artificial Sequence
<220> FEATURE:
<223> OTHER INFORMATION: Synthetic (Light chain variable region of
      anti-Ang2 antibody 8-A5)

<400> SEQUENCE: 63

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 64
<211> LENGTH: 111
<212> TYPE: PRT
<213> ORGANISM: Artificial Sequence
<220> FEATURE:
<223> OTHER INFORMATION: Synthetic (Light chain variable region of
      anti-Ang2 antibody 7-C9)

<400> SEQUENCE: 64

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Asp Val Tyr Trp Tyr Gln Gln Leu Pro Gly Thr Ala Pro Lys Leu Leu
        35                  40                  45

Ile Tyr Ala Asn Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 65
<211> LENGTH: 111
<212> TYPE: PRT
<213> ORGANISM: Artificial Sequence
<220> FEATURE:
<223> OTHER INFORMATION: Synthetic (Light chain variable region of
      anti-Ang2 antibody 4-C11)

<400> SEQUENCE: 65

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ser Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 66
<211> LENGTH: 111
<212> TYPE: PRT
<213> ORGANISM: Artificial Sequence
<220> FEATURE:
<223> OTHER INFORMATION: Synthetic (Light chain variable region of
      anti-Ang2 antibody 4-F5)

<400> SEQUENCE: 66

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ala Val Asn Trp Tyr Gln Gln Leu Pro Gly Thr Ala Pro Lys Leu Leu
        35                  40                  45

Ile Tyr Ala Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 67
<211> LENGTH: 111
<212> TYPE: PRT
<213> ORGANISM: Artificial Sequence
<220> FEATURE:
<223> OTHER INFORMATION: Synthetic (Light chain variable region of
      anti-Ang2 antibody 4-F11)

<400> SEQUENCE: 67

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Asn Asn
            20                  25                  30

Ala Val Ser Trp Tyr Gln Gln Leu Pro Gly Thr Ala Pro Lys Leu Leu
        35                  40                  45

Ile Tyr Ser Asp Ser Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Ala Tyr Val Phe Gly Gly Gly Thr Lys Leu Thr Val Leu Gly
            100                 105                 110
```

<210> SEQ ID NO 68
<211> LENGTH: 111
<212> TYPE: PRT
<213> ORGANISM: Artificial Sequence
<220> FEATURE:
<223> OTHER INFORMATION: Synthetic (Light chain variable region of
      anti-Ang2 antibody 4-H10)

<400> SEQUENCE: 68

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Ala Asp Ser Asn Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly
            100                 105                 110
```

<210> SEQ ID NO 69
<211> LENGTH: 111
<212> TYPE: PRT
<213> ORGANISM: Artificial Sequence
<220> FEATURE:
<223> OTHER INFORMATION: Synthetic (Light chain variable region of
      anti-Ang2 antibody 3-D3)

<400> SEQUENCE: 69

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45
```

```
Ile Tyr Ser Asp Asn Lys Arg Pro Ser Gly Val Pro Asp Arg Phe Ser
 50                  55                  60
Gly Ser Lys Ser Gly Thr Ser Ala Ser Leu Ala Ile Ser Gly Leu Arg
 65                  70                  75                  80
Ser Glu Asp Glu Ala Asp Tyr Tyr Cys Gly Thr Trp Asp Asp Ser Leu
                 85                  90                  95
Asn Gly Tyr Val Phe Gly Gly Gly Thr Lys Leu Thr Val Leu Gly
            100                 105                 110
```

<210> SEQ ID NO 70
<211> LENGTH: 496
<212> TYPE: PRT
<213> ORGANISM: Artificial Sequence
<220> FEATURE:
<223> OTHER INFORMATION: Synthetic (human Ang2)
<220> FEATURE:
<221> NAME/KEY: UNSURE
<222> LOCATION: (417)..(434)
<223> OTHER INFORMATION: Loop 1
<220> FEATURE:
<221> NAME/KEY: UNSURE
<222> LOCATION: (447)..(454)
<223> OTHER INFORMATION: Loop 2
<220> FEATURE:
<221> NAME/KEY: UNSURE
<222> LOCATION: (460)..(468)
<223> OTHER INFORMATION: Loop 3

<400> SEQUENCE: 70

```
Met Trp Gln Ile Val Phe Phe Thr Leu Ser Cys Asp Leu Val Leu Ala
  1               5                  10                  15
Ala Ala Tyr Asn Asn Phe Arg Lys Ser Met Asp Ser Ile Gly Lys Lys
                 20                  25                  30
Gln Tyr Gln Val Gln His Gly Ser Cys Ser Tyr Thr Phe Leu Leu Pro
             35                  40                  45
Glu Met Asp Asn Cys Arg Ser Ser Ser Ser Pro Tyr Val Ser Asn Ala
 50                  55                  60
Val Gln Arg Asp Ala Pro Leu Glu Tyr Asp Asp Ser Val Gln Arg Leu
 65                  70                  75                  80
Gln Val Leu Glu Asn Ile Met Glu Asn Asn Thr Gln Trp Leu Met Lys
                 85                  90                  95
Leu Glu Asn Tyr Ile Gln Asp Asn Met Lys Lys Glu Met Val Glu Ile
            100                 105                 110
Gln Gln Asn Ala Val Gln Asn Gln Thr Ala Val Met Ile Glu Ile Gly
        115                 120                 125
Thr Asn Leu Leu Asn Gln Thr Ala Glu Gln Thr Arg Lys Leu Thr Asp
130                 135                 140
Val Glu Ala Gln Val Leu Asn Gln Thr Thr Arg Leu Glu Leu Gln Leu
145                 150                 155                 160
Leu Glu His Ser Leu Ser Thr Asn Lys Leu Glu Lys Gln Ile Leu Asp
                165                 170                 175
Gln Thr Ser Glu Ile Asn Lys Leu Gln Asp Lys Asn Ser Phe Leu Glu
            180                 185                 190
Lys Lys Val Leu Ala Met Glu Asp Lys His Ile Ile Gln Leu Gln Ser
        195                 200                 205
Ile Lys Glu Glu Lys Asp Gln Leu Gln Val Leu Val Ser Lys Gln Asn
210                 215                 220
Ser Ile Ile Glu Glu Leu Glu Lys Lys Ile Val Thr Ala Thr Val Asn
225                 230                 235                 240
```

Asn Ser Val Leu Gln Lys Gln Gln His Asp Leu Met Glu Thr Val Asn
            245                 250                 255

Asn Leu Leu Thr Met Met Ser Thr Ser Asn Ser Ala Lys Asp Pro Thr
        260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
        290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Gly Asn Glu Ala Tyr
370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
        450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 71
<211> LENGTH: 381
<212> TYPE: DNA
<213> ORGANISM: Artificial Sequence
<220> FEATURE:
<223> OTHER INFORMATION: Synthetic (Polynucleotide encoding heavy chain
      variable region of anti-Ang2 antibody 2-E6)

<400> SEQUENCE: 71
gaagtgcagc ttctggaatc aggcggtgga ctggtgcagc caggaggcag cctcaggctg      60
tcttgcgcag ccagcggatt taccttctcc gattacgcca tgagctgggt tagacaggcc     120
cctggcaagg ggctggagtg ggtcagtgcc atttaccccg actccgggaa taagtattac     180
gctgactctg tgaaaggtag attcactatc tcaagagaca actccaaaaa tacattgtac     240
ttacagatga actcactgcg cgctgaggat acagcagtgt attattgtgc gcggcactcg     300
agtgatccta aggtcaaaag cggatactat gacgacggca tggatgtttg gggccaaggg     360
actctcgtaa ccgtgtcttc t                                               381

<210> SEQ ID NO 72
<211> LENGTH: 333
<212> TYPE: DNA
<213> ORGANISM: Artificial Sequence
<220> FEATURE:

<223> OTHER INFORMATION: Synthetic (Polyucleotide encoding light chain
variable region of anti-Ang2 antibody 2-E6)

<400> SEQUENCE: 72

```
cagtcagtcc tgacacagcc ccctagtgct tccggaaccc ctgggcagag ggtgaccatc        60
tcatgctcag gtagctccag caacattgga acaatgcag ttaattggta tcagcaactg        120
cccgggaccg ccccaaagct tctgatctac gctgatagta atagaccatc tggagtgcct      180
gacagattca gtggttcgaa agcggcact tctgcatcct tggccatttc tggcttaaga       240
tctgaagatg aggccgacta ttactgtggc tcttgggact actccctgag cggatatgtg       300
tttgggggcg gaactaagct cacagtccta ggc                                   333
```

<210> SEQ ID NO 73
<211> LENGTH: 363
<212> TYPE: DNA
<213> ORGANISM: Artificial Sequence
<220> FEATURE:
<223> OTHER INFORMATION: Synthetic (Polyucleotide encoding heavy chain
variable region of anti-Ang2 antibody 8-A5)

<400> SEQUENCE: 73

```
gaggtccagc tgctcgaatc aggcggtggg ctggtgcagc caggcggctc cctgaggtta       60
agttgcgccg cttctggctt acatttagc gattattaca tgtcctgggt ccgccaggcc       120
cccgggaaag gtctggagtg ggtgagcgga atttacccttt ccggggaag cacctattac      180 gcggattctg taaagggtag attcactatc tcaagagaca attctaagaa taccctgtat      240
ttgcagatga acagtcttag agccgaagac acagcagttt attattgtgc aagagacccc      300
agtactctaa cctacgctgg cttcgattac tggggacaag aacgctcgt gacagtgtca      360 agc                                                                    363
```

<210> SEQ ID NO 74
<211> LENGTH: 333
<212> TYPE: DNA
<213> ORGANISM: Artificial Sequence
<220> FEATURE:
<223> OTHER INFORMATION: Synthetic (Polyucleotide encoding light chain
variable region of anti-Ang2 antibody 8-A5)

<400> SEQUENCE: 74

```
caaagtgttc tcacacagcc gccatccgct tccgggaccc ctggacagag agtgaccatc       60
agttgtagtg gctcttcgag caatattggc aataactatg tgacatggta tcagcagctt      120
cctggaacag cccccaaact gctcatctat gccgacagcc acagaccatc aggtgtcccc      180
gatagatttt ctgggtcaaa gtcaggaact agcgcaagcc tggccatttc tggattaagg      240
tccgaggaca agctgattac tattgcgca acttgggact actctctgtc tggttacgtg       300
ttcggcggcg gaaccaagtt gacggtccta ggc                                   333
```

<210> SEQ ID NO 75
<211> LENGTH: 381
<212> TYPE: DNA
<213> ORGANISM: Artificial Sequence
<220> FEATURE:
<223> OTHER INFORMATION: Synthetic (Polyucleotide encoding heavy chain
variable region of anti-Ang2 antibody 7-C9)

<400> SEQUENCE: 75

```
gaggtgcaac tcctggagtc aggaggcggc ctggtccagc ccggcgggag tcttagactc       60
tcgtgtgccg caagcgggtt tacattcagt aactacgcca tgtcctgggt cagacaggct      120
```

```
cctggaaagg gactggaatg ggtttctgcc attagctccg gcggaggtaa tatctattac    180
gctgattccg ttaaagggag gtttacaatc tctcgggata cagcaaaaa tactttgtat    240 ctgcagatga atagcttaag agccgaagac actgcagtgt actactgcgc gaagagcggt    300
attcaaccct ctccaccatc catgtcatca gcttatgcaa tggacgtatg ggggcagggc    360
accctggtga ccgtgagttc t                                              381

<210> SEQ ID NO 76
<211> LENGTH: 333
<212> TYPE: DNA
<213> ORGANISM: Artificial Sequence
<220> FEATURE:
<223> OTHER INFORMATION: Synthetic (Polyucleotide encoding light chain
      variable region of anti-Ang2 antibody 7-C9)

<400> SEQUENCE: 76
cagagcgtcc tgacacaacc tccatccgct tctgggacgc ctggacagag agtgacaatt    60
tcttgcagcg gctcatcttc aaatattgga acaatgacg tttattggta ccagcagctc    120
ccagggaccg ccccaaagct gctgatctat gcaaactcac acagaccag cggagtgccc    180 gatagattca gtggatccaa atccggcact agtgccagct ggcaatctc ggggctgaga    240 tctgaagacg aggctgatta ctattgtggt acctgggatt actccttaag tggttacgtg    300
tttggcgggg gcactaagct taccgtccta ggc                                 333

<210> SEQ ID NO 77
<211> LENGTH: 381
<212> TYPE: DNA
<213> ORGANISM: Artificial Sequence
<220> FEATURE:
<223> OTHER INFORMATION: Synthetic (Polyucleotide encoding heavy chain
      variable region of anti-Ang2 antibody 4-C11)

<400> SEQUENCE: 77
gaagtacagc tgctggagtc gggtggtgga ctggttcagc caggaggctc attaaggctg    60
agctgcgccg caagcggttt cacttttttct gattatgcta tgtcctgggt cagacaggcc    120
cctgggaagg gactcgagtg ggtctcaagt atttaccccg acgatggaaa tacctactat    180
gccgatagcg tgaaggggcg ctttacaatc tctagagata attctaaaaa cccctgtac    240 cttcaaatga actcattgcg ggcagaagac acagcggtgt actattgtgc tagacacacg    300
tcccaccata ccagcatcga cggctactat tattacggga tggacggctg gggccaggc    360 actctcgtga cagtgtccag t                                              381

<210> SEQ ID NO 78
<211> LENGTH: 333
<212> TYPE: DNA
<213> ORGANISM: Artificial Sequence
<220> FEATURE:
<223> OTHER INFORMATION: Synthetic (Polyucleotide encoding light chain
      variable region of anti-Ang2 antibody 4-C11)

<400> SEQUENCE: 78
cagtcagtcc tgactcagcc accctccgca agcgggacac ctggacaaag agttactatc    60
tcttgcaccg ggtcaagctc caatatcggt aacaatgatg tgagttggta ccagcagtta    120
ccaggcaccg ccccgaaact gcttatttac tcagacagca aaagaccctc tggcgtgcct    180
gacagattct caggaagcaa gagtggcacg tctgcttcct tggccattc gggtctgaga    240 tccgaggacg aagctgatta ttattgtgga agctgggatt atagtctgtc tggctacgtg    300
```

```
tttggggcg gaaccaagct cacagtccta ggc                                 333
```

<210> SEQ ID NO 79
<211> LENGTH: 387
<212> TYPE: DNA
<213> ORGANISM: Artificial Sequence
<220> FEATURE:
<223> OTHER INFORMATION: Synthetic (Polyucleotide encoding heavy chain
      variable region of anti-Ang2 antibody 4-F5)

<400> SEQUENCE: 79

```
gaggtgcagt tgctcgagtc cggggtggc ctggtgcagc caggaggaag cctgagactg      60
agctgcgcag cctcaggttt cacattctcc gattacgaca tgtcctgggt taggcaagcc    120
cccggcaagg ggctggaatg ggtaagctct atcagccacg gcgacagtaa caaatattat    180
gcagactctg ttaagggacg gtttaccatt tcacgcgata actcaaagaa tacactgtac    240
cttcaaatga atagtctcag agctgaagat accgccgtgt attactgtgc taaatcgtcc    300
ggaatccagg agagtccccc tactattac tactatggga tggatgtgtg gggccagggc    360
accctggtca ctgtctcttc tgctagc                                        387
```

<210> SEQ ID NO 80
<211> LENGTH: 333
<212> TYPE: DNA
<213> ORGANISM: Artificial Sequence
<220> FEATURE:
<223> OTHER INFORMATION: Synthetic (Polyucleotide encoding light chain
      variable region of anti-Ang2 antibody 4-F5)

<400> SEQUENCE: 80

```
cagtctgtgt tgacccagcc ccctctgca tctggcaccc ccggacagag agtcactata      60
agttgttctg gtagctccct aaatatcggg tcaaacgccg tgaattggta ccagcaatta    120
ccaggaacag ctcctaagct gcttatctat gcagacagta acagaccaag cggcgttcct    180
gatagattct caggctccaa gtccgggact agtgcctcgc tggctattag cggtctcaga    240
agtgaagatg aggccgatta ctattgcgga agctgggact actccctgag cggctatgtg    300
tttggaggag ggacaaaact caccgtccta ggc                                 333
```

<210> SEQ ID NO 81
<211> LENGTH: 381
<212> TYPE: DNA
<213> ORGANISM: Artificial Sequence
<220> FEATURE:
<223> OTHER INFORMATION: Synthetic (Polyucleotide encoding heavy chain
      variable region of anti-Ang2 antibody 4-F11)

<400> SEQUENCE: 81

```
gaggtgcaac tgctggagag tggtgggggc cttgttcagc ccggcggatc cttgaggctg      60
tcatgcgctg cgtctggctt tactttcagc gattacgcaa tgagttgggt gagacaggct    120
ccaggaaaag gcctggaatg ggtcagctcc atttatcctg acgatggtaa cacatattac    180
gccgacagcg taaaaggacg gttcaccatc tctcgcgata attctaagaa caccctgtat    240
ctccagatga atagcctgag agcagaagac accgccgtgt actactgtgc caagcatcct    300
gtgagattaa acctgcaccc aatgtactat tattacggca tggacgtttg ggggcagggg    360
acactcgtga ctgtctcctc a                                              381
```

<210> SEQ ID NO 82
<211> LENGTH: 333

<212> TYPE: DNA
<213> ORGANISM: Artificial Sequence
<220> FEATURE:
<223> OTHER INFORMATION: Synthetic (Polyucleotide encoding light chain
      variable region of anti-Ang2 antibody 4-F11)

<400> SEQUENCE: 82
cagtctgtgt taacacaacc tccaagtgca tccggaacgc cgggccagag agtgactatc      60
agctgcaccg gcagctcgtc caatatcggt aacaacgcag ttagttggta ccagcagctt     120
cccggcacag ctccaaagct cttgatttac agcgattcac aaagacctag tggtgtcccc     180
gatagatttt ctgggagtaa gagcgggacc agtgcctccc tggctatatc aggactgaga     240
tctgaagatg aggctgacta ttactgtgcc acttgggact attcactctc tgcctatgtg     300
ttcgggggcg gaaccaaact gacagtccta ggc                                  333

<210> SEQ ID NO 83
<211> LENGTH: 363
<212> TYPE: DNA
<213> ORGANISM: Artificial Sequence
<220> FEATURE:
<223> OTHER INFORMATION: Synthetic (Polyucleotide encoding heavy chain
      variable region of anti-Ang2 antibody 4-H10)

<400> SEQUENCE: 83
gaggttcagt tgctggagag tggcggcggc ttagtgcagc caggtggcag cctgcgcctt      60
tcttgtgccg ccagtgggtt taccttctcc tcctacgaca tgagctgggt gcggcaggct     120
cccggcaaag gtcttgaatg ggtgtcactg atcagccctg acagttcctc aatctattat     180
gcagattcag tcaagggaag atttaccata agcagagata attccaagaa tactctgtac     240
ctacagatga actcgctcag agccgaagat accgcagtct actactgcgc taaagacctg     300
atttctttct ggagggggggg attcgactat tgggggcaag aacactcgt aacagtgtct     360 agc                                                                   363

<210> SEQ ID NO 84
<211> LENGTH: 333
<212> TYPE: DNA
<213> ORGANISM: Artificial Sequence
<220> FEATURE:
<223> OTHER INFORMATION: Synthetic (Polyucleotide encoding light chain
      variable region of anti-Ang2 antibody 4-H10)

<400> SEQUENCE: 84
cagagcgtgc tcacccaacc tcccagtgca tccggaacgc ctggtcagag agtgacaatt      60
agctgctcag ggtcttcctc taacatcggg tccaattatg tcaattggta tcagcagttg     120
ccaggtacag ctcccaaaact gctgatctac agtgattccc acagacctag cggcgttcca     180
gacagattta gcggatccaa gtcgggaact tctgcaagcc tcgctatttc tggcctgaga     240
agtgaggacg aagccgatta ttactgtggg gcctgggacg attcattatc aggatacgtg     300
ttcggaggcg gcaccaagct tactgtccta ggc                                  333

<210> SEQ ID NO 85
<211> LENGTH: 381
<212> TYPE: DNA
<213> ORGANISM: Artificial Sequence
<220> FEATURE:
<223> OTHER INFORMATION: Synthetic (Polyucleotide encoding heavy chain
      variable region of anti-Ang2 antibody 3-D3)

<400> SEQUENCE: 85

```
gaggtacagc tgctggaaag tgggggcggt ctggtgcagc caggggga ag cctccggctt    60 tcatgcgccg caagcggctt tacattcagt gactatgaca tgagttgggt ccgacaagcc   120
cccggaaagg gcctggagtg ggtgtctgga atctcctccg atgacggcaa tacttattac   180
gctgactccg ttaaaggtag gttcaccatc tctcgcgata actctaaaaa caccctctac   240
ctgcagatga atagcttgag ggcagaagat acggctgtct actattgtgc cagacctaca   300
attgacaagt acacattaag agggtattat tcatacggca tggatgtttg gggacaggga   360
actctagtga ccgtgtccag c                                             381
```

```
<210> SEQ ID NO 86
<211> LENGTH: 333
<212> TYPE: DNA
<213> ORGANISM: Artificial Sequence
<220> FEATURE:
<223> OTHER INFORMATION: Synthetic (Polyucleotide encoding light chain
      variable region of anti-Ang2 antibody 3-D3)

<400> SEQUENCE: 86
```

```
cagtcagtgc tgacacagcc tccaagcgct tccgggacac ctggacaaag agttaccatt    60
tcgtgcaccg gatcctcctc aaacatcggt agcaattatg tgtcttggta ccagcagctc   120
cccgggactg cccccaaact cttgatctac agcgacaaca agagaccatc tggtgtgcct   180
gatagattca gtgggagtaa gtcaggaacg agtgcctctc tggctatttc tggcctgaga   240
agcgaagatg aggcagacta ttattgtggc acctgggatg actccctgaa tggctacgtc   300
tttggcggcg gaacaaaact tactgtccta ggc                                333
```

```
<210> SEQ ID NO 87
<211> LENGTH: 19
<212> TYPE: DNA
<213> ORGANISM: Artificial Sequence
<220> FEATURE:
<223> OTHER INFORMATION: Synthetic (pC3X-f primer)

<400> SEQUENCE: 87
gcacgacagg tttcccgac                                                 19
```

```
<210> SEQ ID NO 88
<211> LENGTH: 20
<212> TYPE: DNA
<213> ORGANISM: Artificial Sequence
<220> FEATURE:
<223> OTHER INFORMATION: Synthetic (pC3X-b primer)

<400> SEQUENCE: 88
aaccatcgat agcagcaccg                                                20
```